(12) United States Patent
Carrasquillo et al.

(10) Patent No.: US 10,875,843 B2
(45) Date of Patent: Dec. 29, 2020

(54) PROCESS FOR PREPARING TETRAHYDROCARBAZOLE CARBOXAMIDE COMPOUND

(71) Applicant: BRISTOL-MYERS SQUIBB COMPANY, Princeton, NJ (US)

(72) Inventors: Ronald Carrasquillo, Somerset, NJ (US); Peng Geng, Hillsborough, NJ (US); Eric C. Huang, Cranbury, NJ (US); Kishta Katipally, Monmouth Junction, NJ (US); Andrew Lee, South San Francisco, CA (US); Boguslaw Mudryk, East Windsor, NJ (US); Xinhua Qian, Highland Park, IL (US); Thomas M. Razler, Yardley, PA (US); Jianji Wang, Dayton, NJ (US); Carolyn S. Wei, Belle Mead, NJ (US); Steven R. Wisniewski, North Brunswick, NJ (US); Ye Zhu, Singapore (SG)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 16/471,020

(22) PCT Filed: Dec. 19, 2017

(86) PCT No.: PCT/US2017/067164
§ 371 (c)(1),
(2) Date: Jun. 19, 2019

(87) PCT Pub. No.: WO2018/118830
PCT Pub. Date: Jun. 28, 2018

(65) Prior Publication Data
US 2020/0109133 A1    Apr. 9, 2020

Related U.S. Application Data

(60) Provisional application No. 62/436,696, filed on Dec. 20, 2016.

(51) Int. Cl.
*C07D 403/10*    (2006.01)

(52) U.S. Cl.
CPC ................... *C07D 403/10* (2013.01)

(58) Field of Classification Search
CPC ..................................... C07D 403/10
See application file for complete search history.

(56) References Cited

U.S. PATENT DOCUMENTS 5,872,273  A    2/1999  Saito et al.

FOREIGN PATENT DOCUMENTS

WO    WO2014210085 A1    12/2014

OTHER PUBLICATIONS

Beutner, et al., "Nickel-Catalyzed Synthesis of Quinasolinediones", Organic Letters, 2017, vol. 19, pp. 1052-1055.
International Preliminary Report on Patentability for PCT/US2017/067164, dated Jul. 25, 2019.
Watterson, et al., "Discovery of 6-Fluoro-5-(R)-(3-(S)-(8-fluoro-1-methyl-2,4-dioxo-1,2-dihydroquinazolin-3(4H)-yl)-2-methylphenyl)-2-(S)-(2)-hydroxypropan-2-yl)-2,3,4,9-tetrahydro-1H-carbezole-8-carboxamide:A Reversible Inhibitor of Bruton's Tyrosine Kinase Conformationally Constrained by Two Locked Atropisomers", Journal of Medicinal Chemistry, 2016, vol. 59 (19). pp. 9173-9200.

*Primary Examiner* — Paul V Ward
(74) *Attorney, Agent, or Firm* — Gary Greenblatt

(57) ABSTRACT

Disclosed is a process for preparing Compound 8: (8) comprising the step of reacting Compound of 7: (7) wherein R is C1-8 alkyl or benzyl in the presence of a base. Also disclosed are intermediates and processes for preparing the intermediates.

6 Claims, 4 Drawing Sheets

PROCESS FOR PREPARING TETRAHYDROCARBAZOLE CARBOXAMIDE COMPOUND

This application is a 371 application of International Application No. PCT/US2017/067164, filed on Dec. 19, 2017, which claims the benefit of U.S. Provisional Patent Application Ser. No. 62/436,696, filed Dec. 20, 2016, the content of each is hereby fully incorporated by reference in its entirety for all purposes.

The present invention generally relates to processes for preparing a tetrahydrocarbazole carboxamide compound.

Protein kinases, the largest family of human enzymes, encompass well over 500 proteins. Btk is a member of the Tec family of tyrosine kinases, and is a regulator of early B-cell development, as well as mature B-cell activation, signaling, and survival.

B-cell signaling through the B-cell receptor (BCR) leads to a wide range of biological outputs, which in turn depend on the developmental stage of the B-cell. The magnitude and duration of BCR signals must be precisely regulated. Aberrant BCR-mediated signaling can cause disregulated B-cell activation and/or the formation of pathogenic auto-antibodies leading to multiple autoimmune and/or inflammatory diseases. Mutation of Btk in humans results in X-linked agammaglobulinaemia (XLA). This disease is associated with the impaired maturation of B-cells, diminished immunoglobulin production, compromised T-cell-independent immune responses and marked attenuation of the sustained calcium signal upon BCR stimulation.

Evidence for the role of Btk in allergic disorders and/or autoimmune disease and/or inflammatory disease has been established in Btk-deficient mouse models. For example, in standard murine preclinical models of systemic lupus erythematosus (SLE), Btk deficiency has been shown to result in a marked amelioration of disease progression. Moreover, Btk deficient mice are also resistant to developing collagen-induced arthritis and are less susceptible to Staphylococcus-induced arthritis.

A large body of evidence supports the role of B-cells and the humoral immune system in the pathogenesis of autoimmune and/or inflammatory diseases. Protein-based therapeutics (such as Rituxan) developed to deplete B-cells, represent an important approach to the treatment of a number of autoimmune and/or inflammatory diseases. Because of Btk's role in B-cell activation, inhibitors of Btk can be useful as inhibitors of B-cell mediated pathogenic activity (such as autoantibody production).

Btk is also expressed in mast cells and monocytes and has been shown to be important for the function of these cells. For example, Btk deficiency in mice is associated with impaired IgE-mediated mast cell activation (marked diminution of TNF-alpha and other inflammatory cytokine release), and Btk deficiency in humans is associated with greatly reduced TNF-alpha production by activated monocytes.

Thus, inhibition of Btk activity can be useful for the treatment of allergic disorders and/or autoimmune and/or inflammatory diseases including, but not limited to: SLE, rheumatoid arthritis, multiple vasculitides, idiopathic thrombocytopenic purpura (ITP), myasthenia gravis, allergic rhinitis, multiple sclerosis (MS), transplant rejection, type I diabetes, membranous nephritis, inflammatory bowel disease, autoimmune hemolytic anemia, autoimmune thyroiditis, cold and warm agglutinin diseases, Evan's syndrome, hemolytic uremic syndrome/thrombotic thrombocytopenic purpura (HUS/TTP), sarcoidosis, Sjögren's syndrome, peripheral neuropathies (e.g., Guillain-Barre syndrome), pemphigus vulgaris, and asthma.

In addition, Btk has been reported to play a role in controlling B-cell survival in certain B-cell cancers. For example, Btk has been shown to be important for the survival of BCR-Abl-positive B-cell acute lymphoblastic leukemia cells. Thus inhibition of Btk activity can be useful for the treatment of B-cell lymphoma and leukemia.

Atropisomers are stereoisomers resulting from hindered rotation about a single bond axis where the rotational barrier is high enough to allow for the isolation of the individual rotational isomers. (LaPlante et al., *J. Med. Chem.* 2011, 54, 7005-7022).

U.S. Pat. No. 9,334,290 discloses substituted tetrahydrocarbazole and carbazole compounds useful as Btk inhibitors, including 6-fluoro-5-(R)-(3-(S)-(8-fluoro-1-methyl-2,4-dioxo-1,2-dihydroquinazolin-3(4H)-yl)-2-methylphenyl)-2-(S)-(2-hydroxypropan-2-yl)-2,3,4,9-tetrahydro-1H-carbazole-8-carboxamide as Example 28. 6-fluoro-5-(R)-(3-(S)-(8-fluoro-1-methyl-2,4-dioxo-1,2-dihydroquinazolin-3(4H)-yl)-2-methylphenyl)-2-(S)-(2-hydroxypropan-2-yl)-2,3,4,9-tetrahydro-1H-carbazole-8-carboxamide, referred to herein as Compound 8, has two stereogenic axes:

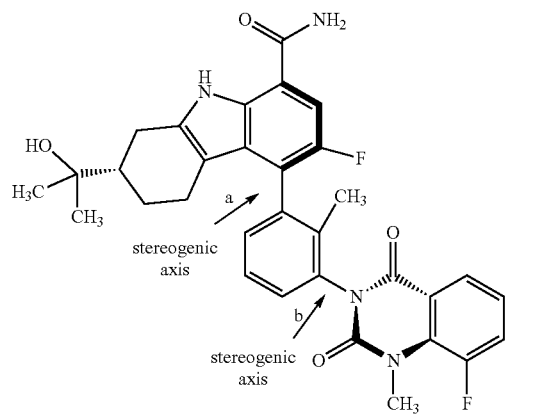

(8)

(i) bond "a" between the tricyclic tetrahydrocarbazole/carbazole group and the phenyl group; and (ii) bond "b" between the substituted tetrahydroquinazolinedione group and the phenyl group. Compound 8 has non-symmetric substitutions on the rings connected by the single bonds labeled "a" and "b", and limited rotation about these bonds caused by steric hindrance. As the rotational energy barriers are sufficiently high, hindered rotations about bond (a) and bond (b) occur at rates that are slow enough to allow isolation of Compound 8 and the other atropisomers of Compound 8 as four individual diastereomeric atropisomer compounds. These four rotational isomers can be separated by chromatography on a stationary phase to provide chiral mixtures of two atropisomers or individual atropisomers.

U.S. Pat. No. 9,334,290 discloses a multistep synthesis process for preparing the Compound 8. This process is shown schematically in FIGS. 2-4. The disclosed process includes three chiral separations from racemic mixtures including (i) a chiral separation of a racemic mixture of chiral enantiomers (FIG. 2); (ii) chiral separation of a mixture of atropisomers along bond "b" between the substituted tetrahydroquinazolinedione group and the phenyl group (FIG. 3); and chiral separation of a mixture of atropisomers along bond "a" between the tricyclic tetrahydrocarbazole/carbazole group and the phenyl group (FIG. 4). In each one of these chiral separations, the maximum yield of the desired enantiomer or atropisomer from the racemic mixture is 50%.

There are difficulties associated with the adaptation of this multistep synthesis disclosed in U.S. Pat. No. 9,334,290 to a larger scale synthesis, such as production in a pilot plant or a manufacturing plant for commercial production. Additionally, it is desired to have a process that provides higher yields and/or reduces waste.

Applicants have discovered a synthesis process for the preparation of Compound 8 that provides higher yields, reduces waste, and/or is adaptable to large scale manufacturing.

SUMMARY OF THE INVENTION

Provided is a process making for preparing 6-fluoro-5-(R)-(3-(S)-(8-fluoro-1-methyl-2,4-dioxo-1,2-dihydroquinazolin-3(4H)-yl)-2-methylphenyl)-2-(S)-(2-hydroxypropan-2-yl)-2,3,4,9-tetrahydro-1H-carbazole-8-carboxamide.

Provided is a process making for preparing (2S)-5-(3-amino-2-methylphenyl)-6-fluoro-2-(2-hydroxypropan-2-yl)-2,3,4,9-tetrahydro-1H-carbazole-8-carboxamide.

Provided is a process making for preparing propyl (2-((3-((2S)-8-carbamoyl-6-fluoro-2-(2-hydroxypropan-2-yl)-2,3,4,9-tetrahydro-1H-carbazol-5-yl)-2-methylphenyl)carbamoyl)-6-fluorophenyl)(methyl)carbamate.

Also provided are intermediates useful in the preparation of (2S)-5-(3-amino-2-methylphenyl)-6-fluoro-2-(2-hydroxypropan-2-yl)-2,3,4,9-tetrahydro-1H-carbazole-8-carboxamide, propyl(2-((3-((2S)-8-carbamoyl-6-fluoro-2-(2-hydroxypropan-2-yl)-2,3,4,9-tetrahydro-1H-carbazol-5-yl)-2-methylphenyl)carbamoyl)-6-fluorophenyl) (methyl) carbamate; or 6-fluoro-5-(R)-(3-(S)-(8-fluoro-1-methyl-2,4-dioxo-1,2-dihydroquinazolin-3(4H)-yl)-2-methylphenyl)-2-(S)-(2-hydroxypropan-2-yl)-2,3,4,9-tetrahydro-1H-carbazole-8-carboxamide.

These and other features of the invention will be set forth in expanded form as the disclosure continues.

BRIEF DESCRIPTION OF THE DRAWINGS

The invention is illustrated by reference to the accompanying drawing described below.

DETAILED DESCRIPTION

Figure 1:
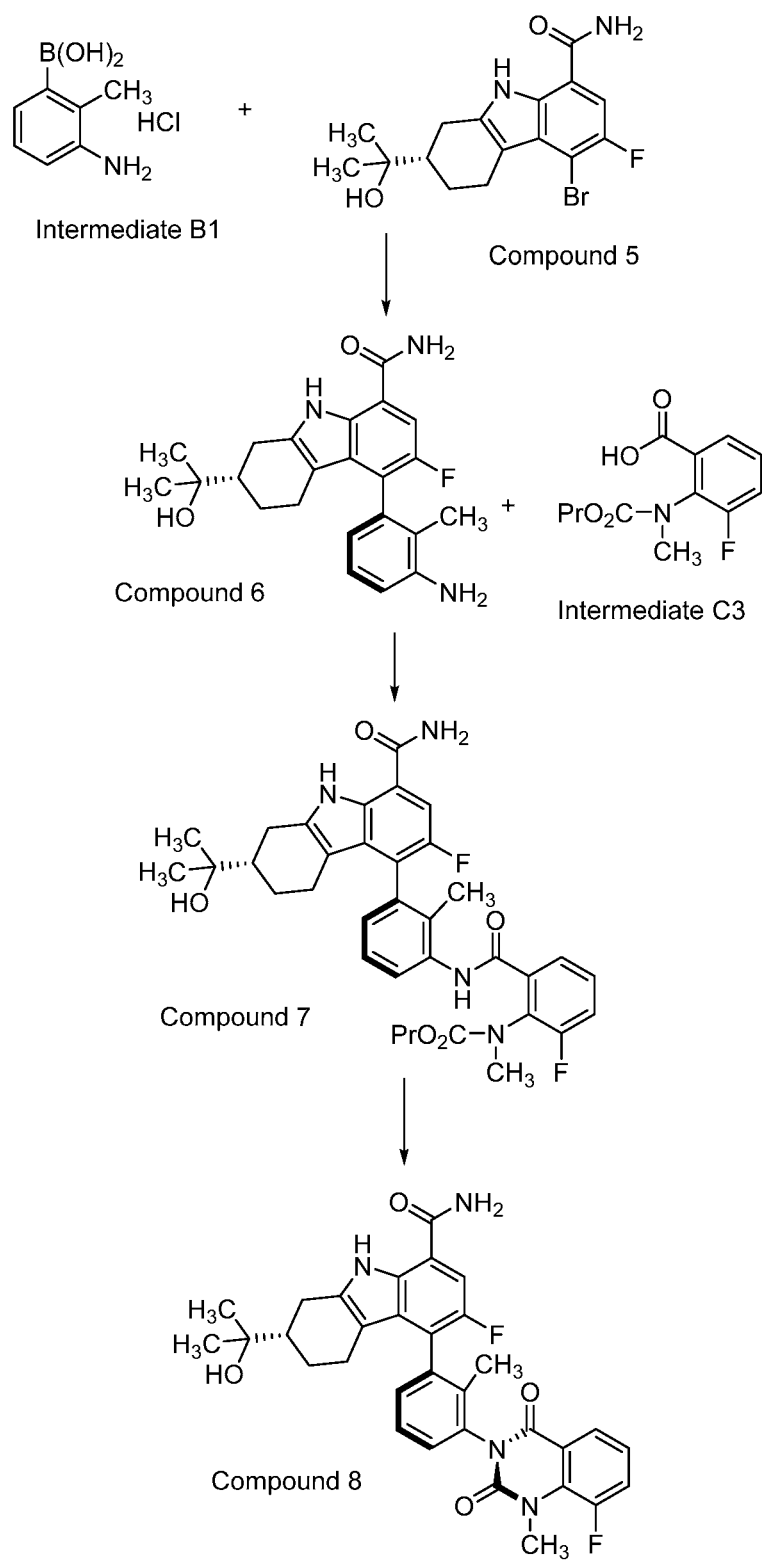
FIG. 1 shows the stereoselective synthesis scheme for the preparation of 6-fluoro-5-(R)-(3-(S)-(8-fluoro-1-methyl-2,4-dioxo-1,2-dihydroquinazolin-3(4H)-yl)-2-methylphenyl)-2-(S)-(2-hydroxypropan-2-yl)-2,3,4,9-tetrahydro-1H-carbazole-8-carboxamide, Compound 8, according to the processes of second aspect, the third aspect, and the first aspect of the invention.
Figure 2:
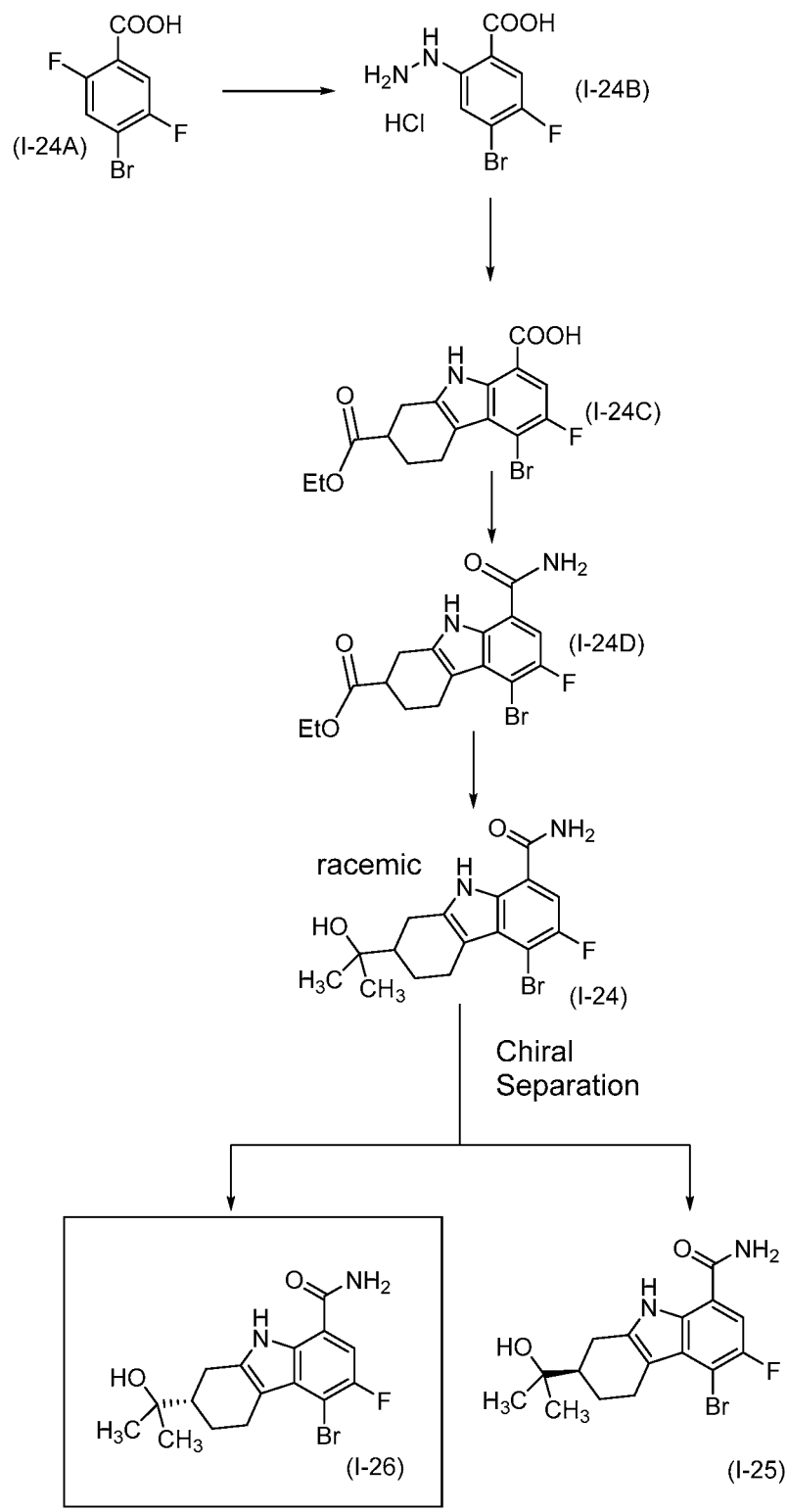
FIG. 2 shows the synthesis scheme disclosed in U.S. Pat. No. 9,334,290 for the preparation of (S)-5-bromo-6-fluoro-2-(2-hydroxypropan-2-yl)-2,3,4,9-tetrahydro-1H-carbazole-8-carboxamide, Compound 5 (Intermediate 26 in U.S. Pat. No. 9,334,290).
Figure 3:
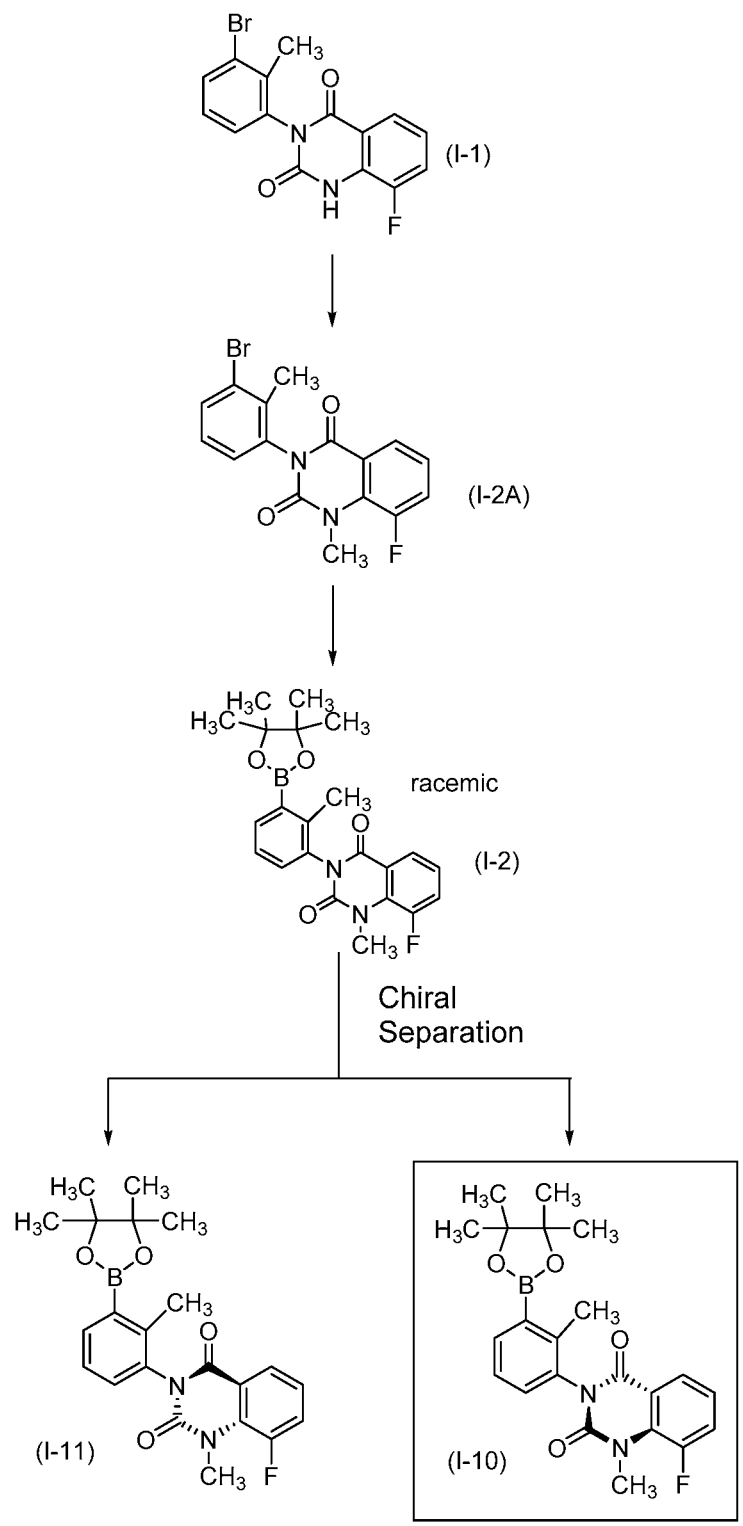
FIG. 3 shows the synthesis scheme disclosed in U.S. Pat. No. 9,334,290 for the preparation of 8-fluoro-1-methyl-3-(S)-(2-methyl-3-(4,4,5,5-tetramethyl-1,3,2-dioxaborolan-2-yl) phenyl)quinazoline-2,4(1H,3H)-dione, Intermediate 10 in U.S. Pat. No. 9,334,290.

The first aspect of the invention provides a process for preparing Compound 8:

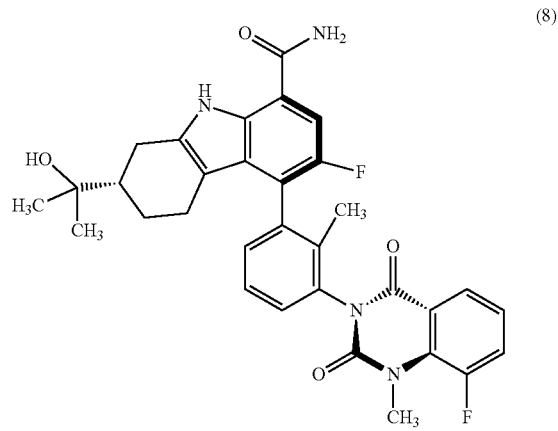

(8)

comprising the step of reacting Compound 7:

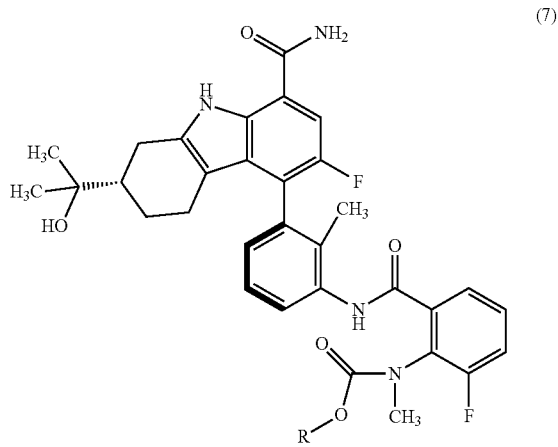

(7)

wherein R is $C_{1-8}$ alkyl or benzyl;
in the presence of:
(i) one or more bases selected from lithium bases, sodium bases, potassium bases, cesium bases, 1,8-diazabicycloundec-7-ene, and 1,1,3,3-tetramethylguanidine; and
(ii) a solvent selected from n-butyl acetate (nBuOAc), cyclopentyl methyl ether (CPME), dimethoxyethane (DME), dimethylacetamide (DMAc), dimethylformamide (DMF), 1,4-dioxane, ethyl acetate (EtOAc), isobutyl acetate (iBuOAc), isopropyl acetate (IPAc), isopropyl alcohol (IPA), methanol (MeOH), methyl acetate (MeOAc), methyl isobutyl ketone (MIBK), N-methyl-2-pyrrolidone (NMP), 2-methyltetrahydrofuran (MeTHF), tetrahydrofuran (THF), tetrahydropyran (THP), and mixtures thereof; to provide said Compound 8.

The second aspect of the invention provides a process for preparing Compound 6:

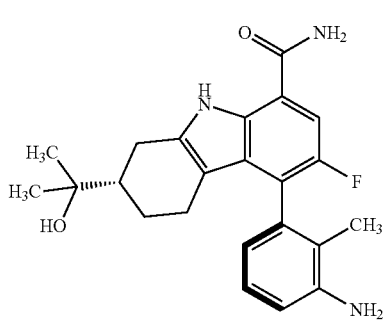
(6)

or a salt thereof, comprising the step of reacting Compound 5 or a salt thereof with Intermediate B1 or a salt thereof:

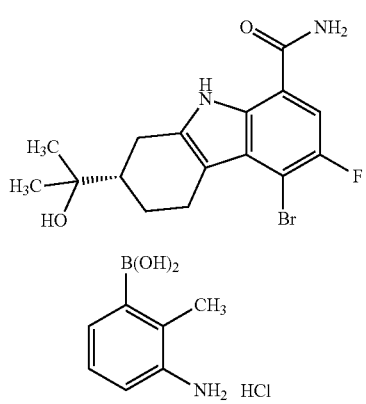
(5)

(B1)

in the presence of:

(i) one or more catalysts selected from palladium(II) acetate (Pd(OAc)$_2$), bis(acetonitrile)dichloropalladium(II) (PdCl$_2$(CH$_3$CN)$_2$), and allylpalladium(II) chloride dimer ([(Allyl)PdCl]$_2$);

(ii) a ligand selected from (R)-(+)-7,7'-bis[di(3,5-dimethylphenyl)phosphino]-1,1'-spirobiindane (Xyl-SDP-R), (R)-(+)-2,2'-bis(di-p-tolylphosphino)-1,1'-binaphthyl (Tol-BINAP-R), (R)-(+)-2,2'-bis[di(3,5-xylyl)phosphino]-1,1'-binaphthyl (Xyl-BINAP-R), (R)-(+)-2,2'-bis (diphenylphosphino)-1,1'-binaphthyl (BINAP-R), (2'-(diphenylphosphino)-[1,1'-binaphthalen]-2-yl) diphenylphosphine oxide (BINAP(O)-R), and bis{2-[(11bR)-3,5-dihydro-4H-dinaphtho[2,1-c: 1',2'-e]phosphepin-4-yl]ethyl}amine (BBNDEA-R);

(iii) a base selected from LiOH, NaOH, KOH, K$_3$PO$_4$, and mixtures thereof;

(iv) an organic solvent selected from methyl tetrahydrofuran, methanol, acetonitrile, dioxane, isopropyl alcohol, t-amyl alcohol, and mixtures thereof; and (v) water;

at a temperature in the range of from about 0 to about 20° C.; to provide said Compound 6 or a salt thereof.

The third aspect of the invention provides a process for preparing Compound 7:

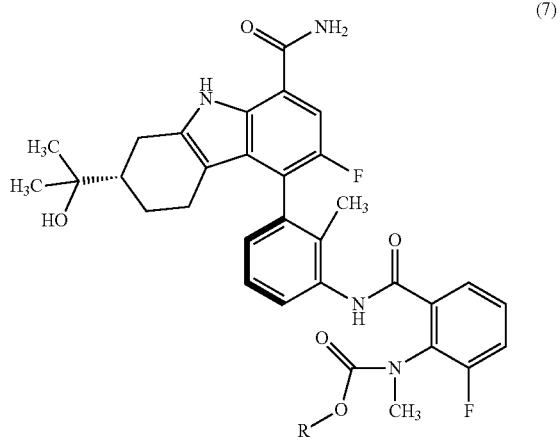
(7)

wherein R is C$_{1-8}$ alkyl or benzyl;

comprising the step of reacting Compound 6 or a salt thereof with Intermediate C3 or a salt thereof:

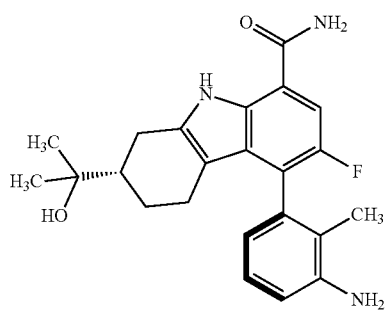
(6)

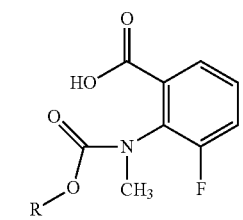
(C3)

in the presence of:

(i) an adjuvant selected from O-(benzotriazol-1-yl)-N,N, N',N'-tetramethyluronium tetrafluoroborate (TBTU), 1-[bis (dimethylamino)methylene]-1H-1,2,3-triazolo[4,5-b]pyridinium 3-oxide hexafluorophosphate (HATU), 1-ethyl-3-(3-dimethylaminopropyl) carbodiimide (EDAC), 2-hydroxypyridine-N-oxide (HOPO), and mixtures thereof;

(ii) a base selected from diisopropylethylamine (DIPEA), 1-methylimidazole, 3,4-lutidine, pyridine, 4-picoline, 2,6-lutidine, dimethylaminopyridine (DMAP), N-methylmorpholine, tributyl amine, N-methylpyrrolidine, and mixtures thereof;

(iii) an acid selected from methanesulfonic acid, ethanesulfonic acid, toluenesulfonic acid, hydrochloric acid, and mixtures thereof, and (iv) a solvent selected from dimethylformamide (DMF), N-methyl-2-pyrrolidone, dimethylacetamide (DMAc), dimethylsulfoxide, tetrahydrofuran, acetonitrile, 2-methyltetrahydrofuran, and mixtures thereof;
at a temperature in the range of from zero to 50° C.; to provide said Compound 7.

The fourth aspect of the invention provides Compound 6 having the structure:

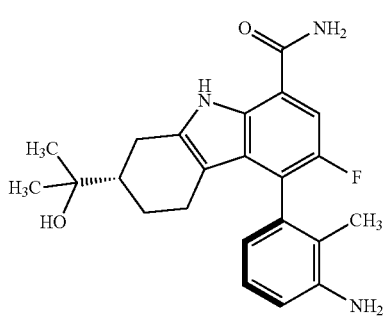

(6)

or a salt thereof.

The fifth aspect of the invention provides Compound 7 having the structure:

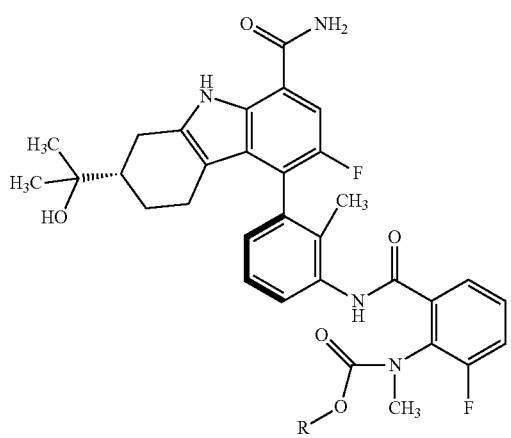

(7)

or a salt thereof, wherein R is $C_{1-8}$ alkyl or benzyl.

The sixth aspect of the invention provides Compound 2 having the structure:

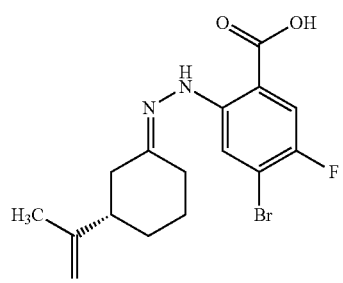

(2)

or a salt thereof.

The seventh aspect of the invention provides Compound 3 having the structure:

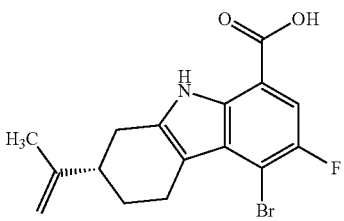

(3)

or a salt thereof.

The eighth aspect of the invention provides Compound 4 having the structure:

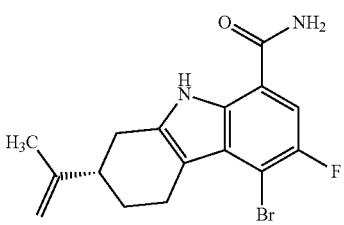

(4)

or a salt thereof.

The ninth aspect of the invention provides Intermediate C3 having the structure:

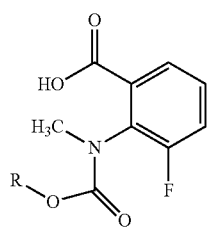

(C3)

or a salt thereof, wherein R is $C_{1-8}$ alkyl or benzyl.

A stereoselective reaction process yields an enriched product mixture having a larger amount of the desired compound compared to its diastereomer or enantiomer. The enriched product mixture can be characterized by the ratio of the desired compound compared to its diastereomer or enantiomer. For example, a stereoselective reaction process yielding an enriched product mixture of 75% desired compound and 25% diastereomer or enantiomer has a selectivity yield of 75% and a selectivity ratio of 3:1. In comparison, a racemic mixture having equal amounts of the desired compound and its diastereomer or enantiomer has a selectivity yield of 50% and a selectivity ratio of 1:1.

The first aspect of the invention is directed towards a stereoselective synthesis process for preparing Compound 8. The process provides stereoselective control of the ring closure step to form the 1,2-dihydroquinazolin-3(4H)-yl) group. In this reaction, the 1,2-dihydroquinazolin-3(4H)-yl) group, which is attached to the phenyl group, is spatially oriented to provide Compound 8 with a greater than 50% yield over its diastereomer. The process is useful for increasing the yield of Compound 8 over its diastereomer, reducing waste, and/or preparing diastereomeric enriched mixtures of Compound 8.

The process of the first aspect is conducted in the presence of one or more bases selected from lithium bases, sodium bases, potassium bases, cesium bases, 1,8-diazabicycloundec-7-ene, and 1,1,3,3-tetramethylguanidine. Examples of suitable lithium bases include lithium propoxide, lithium tert-butoxide, lithium silanolate, lithium tetramethylpiperidide (LiTMP), lithium amide (LiNH$_2$), lithium thioethoxide (LiSEt), lithium phenoxide, lithium diisopropylamide (LDA), lithium dicyclohexylamine (LiNCy$_2$), lithium diphenylphosphide (LiPPh$_2$), lithium ethoxide, lithium methoxide, lithium hydroxide, lithium oxide, lithium borohydride, lithium iso-propoxide, lithium acetylide ethylenediamine, lithium (dimethylamino)trihydroborate, lithium pyrrolidinoborohydride, and 2,2,6,6-tetramethylpiperidinylmagnesium chloride lithium chloride complex (TMPMgCl-LiCl). Examples of suitable sodium bases include sodium propoxide, sodium tert-butoxide, sodium silanolate, sodium bis (trimethylsilyl)amide (NaHMDS), sodium amide (NaNH$_2$), and sodium hydride. Examples of suitable potassium bases include potassium propoxide, potassium tert-butoxide, potassium tert-pentoxide, potassium silanolate, potassium bis(trimethylsilyl)amide (KHMDS), and potassium phosphate, tribasic, and potassium phosphate, tribasic. Examples of suitable cesium bases include cesium carbonate, cesium hydroxide, cesium bicarbonate, cesium chloride, cesium bromide, cesium iodide, cesium 2-ethylhexoxide, and cesium methoxide.

In one embodiment, the process of the first aspect is conducted in the presence of one or more bases selected from lithium t-butoxide, lithium pyrrolidinoborohydride, lithium isopropoxide, lithium (dimethylamino)trihydroborate, lithium acetylide, ethylenediamine, LiNH$_2$, lithium borohydride, LiSEt, lithium phenoxide, lithium silanolate, LDA, LiNCy$_2$, lithium oxide, LiTMP, LiPPh$_2$, lithium hydroxide, lithium methoxide, lithium ethoxide, NaHMDS, sodium hydride, sodium silanolate, potassium phosphate, tribasic, and sodium t-butoxide.

In one embodiment, the process of the first aspect is conducted in the presence of one or more bases selected from lithium t-butoxide, lithium pyrrolidinoborohydride, lithium isopropoxide, lithium (dimethylamino)trihydroborate, lithium acetylide ethylenediamine, LiNH$_2$, lithium borohydride, LiSEt, lithium phenoxide, lithium silanolate, LDA, LiNCy$_2$, lithium oxide, LiTMP, LiPPh$_2$, lithium hydroxide, lithium methoxide, and lithium ethoxide. Included in this embodiment is the process of the first aspect wherein said process is conducted in the presence of one or more bases selected from lithium t-butoxide, lithium pyrrolidinoborohydride, lithium isopropoxide, lithium (dimethylamino)trihydroborate, lithium acetylide ethylenediamine, LiNH$_2$, lithium borohydride, LiSEt, lithium phenoxide, lithium silanolate, LDA, LiNCy$_2$, lithium oxide, and LiTMP. Also included in this embodiment is the process of the first aspect wherein said process is conducted in the presence of one or more bases selected from lithium t-butoxide, lithium pyrrolidinoborohydride, lithium isopropoxide, lithium (dimethylamino)trihydroborate, lithium acetylide, ethylenediamine, LiNH$_2$, and lithium borohydride.

In one embodiment, the process of the first aspect is conducted in the presence of one or more bases selected from lithium t-butoxide, lithium pyrrolidinoborohydride, lithium isopropoxide, lithium (dimethylamino)trihydroborate, and lithium acetylide ethylenediamine. Included in this embodiment is the process of the first aspect wherein said process is conducted in the presence of one or more bases selected from lithium t-butoxide and lithium pyrrolidinoborohydride. Also included in this embodiment is the process of the first aspect wherein said process is conducted in the presence of lithium pyrrolidinoborohydride. Additionally, included in this embodiment is the process of the first aspect wherein said process is conducted in the presence of lithium t-butoxide.

Suitable amounts of base for the process of the first aspect include from about 0.04 to about 1 equivalent, from about 0.04 to about 0.20 equivalent, and from about 0.04 to about 0.06 equivalent, based on Compound 7.

The process of the first aspect is conducted in the presence of a solvent selected from n-butyl acetate (nBuOAc), cyclopentyl methyl ether (CPME), dimethoxyethane (DEM), dimethylacetamide (DMAc), dimethylformamide (DMF), 1,4-dioxane, ethyl acetate (EtOAc), isobutyl acetate (iBuOAc), isopropyl alcohol (IPA), isopropyl acetate (IPAc), methanol (MeOH), methyl acetate (MeOAc), methyl isobutyl ketone (MIBK), N-methyl-2-pyrrolidone (NMP), 2-methyltetrahydrofuran (MeTHF), tetrahydrofuran (THF), tetrahydropyran (THP), and mixtures thereof. Suitable amounts of solvent include from about 10 to about 48 liters of solvent, from about 20 to about 48 liters of solvent, and from about 25 to about 40 liters of solvent, per kilogram of starting material.

In one embodiment, the process of the first aspect is conducted in the presence of a solvent selected from n-butyl acetate (nBuOAc), cyclopentyl methyl ether (CPME), 1,4-dioxane, ethyl acetate (EtOAc), isobutyl acetate (iBuOAc), isopropyl acetate (IPAc), 2-methyltetrahydrofuran (MeTHF), tetrahydrofuran (THF), tetrahydropyran (THP), and mixtures thereof. Included in this embodiment is the process of the first aspect wherein said process is conducted in the presence of a solvent selected from cyclopentyl methyl ether (CPME), 1,4-dioxane, 2-methyltetrahydrofuran (MeTHF), tetrahydrofuran (THF), tetrahydropyran (THP), and mixtures thereof. Also included in this embodiment is the process of the first aspect wherein said process is conducted in the presence of a solvent selected from 1,4-dioxane, MeTHF, THP, and mixtures thereof. Additionally, included in this embodiment is the process of the first aspect wherein said process is conducted in the presence of 1,4-dioxane and MeTHF.

In one embodiment, the process of the first aspect is conducted in the presence of a solvent selected from 1,4-dioxane.

In one embodiment, the process of the first aspect is conducted in the presence of a solvent selected from 2-methyltetrahydrofuran.

In one embodiment, the process of the first aspect is conducted in the presence of a solvent mixture comprising 1,4-dioxane and a second solvent selected from CPME, IPAc, DEM, EtOAc, iBuOAc, IPA, MeTHF, MIBK, nBuOAc, and THF.

In one embodiment, the process of the first aspect is conducted in the presence of (i) a base selected from lithium tert-butoxide; and (ii) a solvent selected from 1,4-dioxane, 2-methyltetrahydrofuran, tetrahydropyran, and mixtures thereof.

Suitable temperatures for the process of the first aspect include temperatures in the range of from about 0° C. to about 50° C., temperatures in the range of from about 10° C. to about 35° C., temperatures in the range of from about 10° C. to about 30° C., temperatures in the range of from about 20° C. to about 30° C., and temperatures in the range of from about 20° C. to about 25° C.

One diastereomer of Compound 8 has the structure:

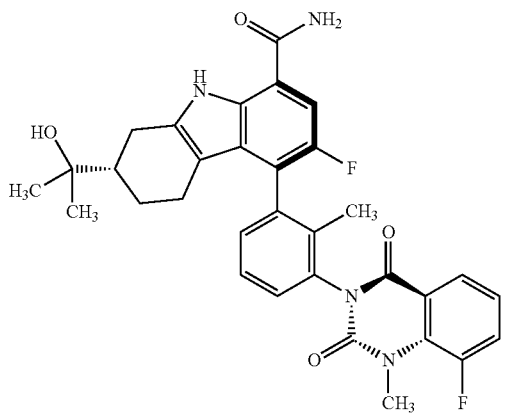

(Diastereomer 1 of Compound 8).

In one embodiment, the process of the first aspect provides an enriched mixture comprising Compound 8 and the Diastereomer 1 of Compound 8 having a selectivity yield of at least 60%, 65%, 70%, 75%, 80%, 85%, 90%, or 95% for Compound 8 compared to Diastereomer 1 of Compound 8.

In one embodiment, the process of the first aspect provides an enriched mixture having a selectivity ratio of at least 3:2, 2:1, 7:3, 3:1, 4:1, 5:1, 9:1, 10:1, 12:1, 15:1, 19:1, and 23:1 for Compound 8 compared to its diastereomer.

One embodiment of the process of the first aspect provides a process for the preparation of Compound 8 from Compound 7 wherein R is $C_{1-8}$ alkyl. Included in this embodiment is a process in which Compound 8 is prepared from Compound 7 wherein R is $C_{2-4}$ alkyl. Also, included in this embodiment is a process in which Compound 8 is prepared from Compound 7 wherein R is ethyl, n-propyl, or n-butyl. Additionally, included is a process in which Compound 8 is prepared from Compound 7 wherein R is n-propyl.

Compound 8 can be isolated and/or purified by various methods known in the art. Suitable methods include crystallization, chromatography, filtration, and distillation.

The second aspect of the invention is a stereoselective coupling reaction. The process provides stereoselective control of the coupling of Intermediate B1 to Compound 5 to provide Compound 6. The substituted phenyl group is spatially oriented to provide Compound 6 with greater than 50% yield over its diastereomer. The process is useful for increasing the yield of Compound 6 over its diastereomer, reducing waste, and/or preparing diastereomeric enriched mixtures of Compound 6.

The diastereomer of Compound 6 has the structure:

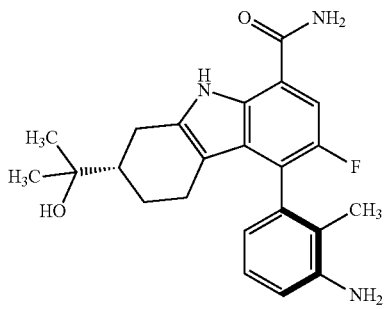

(diastereomer of Compound 6).

The process of the second aspect of the invention is conducted in the presence of one or more catalysts selected from palladium(II) acetate, allylpalladium(II) chloride dimer, and bis(acetonitrile)dichloropalladium(II).

In one embodiment, the process of the second aspect is conducted in the presence of a catalyst selected from palladium(II) acetate, bis(acetonitrile)dichloropalladium(II), and allylpalladium(II) chloride dimer.

In one embodiment, the process of the second aspect is conducted in the presence of a catalyst selected from palladium(II) acetate. Suitable catalyst amounts include 5 mol % $Pd(OAc)_2$, based on the amount of Compound 5.

Suitable amounts of catalyst for the process of the second aspect include from about 0.045 to about 0.055 mol/mol, from about 0.047 to about 0.053 mol/mol, and from about 0.049 to about 0.051 mol/mol, based on Compound 5.

In one embodiment, the process of the second aspect is conducted in the presence of a catalyst selected from allylpalladium(II) chloride dimer.

The process of the second aspect of the invention is conducted in the presence of a ligand selected from (R)-(+)-7,7'-bis[di(3,5-dimethylphenyl)phosphino]-1,1'-spirobiindane, (R)-(+)-2,2'-bis(di-p-tolylphosphino)-1,1'-binaphthyl, (R)-(+)-2,2'-bis[di(3,5-xylyl)phosphino]-1,1'-binaphthyl, (R)-(+)-2,2'-bis(diphenylphosphino)-1,1'-binaphthyl, (2'-(diphenylphosphino)-[1,1'-binaphthalen]-2-yl)diphenylphosphine oxide, and bis{2-[(11bR)-3,5-dihydro-4H-dinaphtho[2,1-c:1',2'-e]phosphepin-4-yl]ethyl}amine.

Suitable amounts of ligand include from about 0.049 to about 0.061 mol/mol, from about 0.052 to about 0.058 mol/mol, and from about 0.054 to about 0.056 mol/mol, based on Compound 5.

In one embodiment, the process of the second aspect is conducted in the presence of a ligand selected from (R)-(+)-2,2'-bis(di-p-tolylphosphino)-1,1'-binaphthyl, (R)-(+)-2,2'-bis[di(3,5-xylyl)phosphino]-1,1'-binaphthyl, (R)-(+)-2,2'-bis(diphenylphosphino)-1,1'-binaphthyl, and (2'-(diphenylphosphino)-[1,1'-binaphthalen]-2-yl) diphenylphosphine oxide.

In one embodiment, the process of the second aspect is conducted in the presence of a ligand selected from (R)-(+)-2,2'-bis(diphenylphosphino)-1,1'-binaphthyl.

In one embodiment, the process of the second aspect is conducted in the presence of a catalyst selected from bis (acetonitrile)dichloropalladium(II).

The process of the second aspect is conducted in the presence of a base selected from LiOH, NaOH, KOH, $K_3PO_4$, and mixtures thereof.

In one embodiment, the process of the second aspect is conducted in the presence of a base selected from NaOH, KOH, $K_3PO_4$, and mixtures thereof.

In one embodiment, the process of the second aspect is conducted in the presence of a base selected from KOH, $K_3PO_4$, and mixtures thereof.

In one embodiment, the process of the second aspect is conducted in the presence of a base selected from KOH.

In one embodiment, the process of the second aspect is conducted in the presence of a base selected from $K_3PO_4$.

Suitable amounts of base in the process of the second aspect include from about 5 to about 7 equivalents, from about 5.5 to about 6.5 equivalents, and from about 5.8 to about 6.2 equivalents, based on the Compound 5.

The process of the second aspect is conducted in the presence of an organic solvent selected from methyl tetrahydrofuran, methanol, acetonitrile, dioxane, isopropyl alcohol, t-amyl alcohol, and mixtures thereof.

In one embodiment, the process of the second aspect is conducted in the presence of an organic solvent selected from methyl tetrahydrofuran, methanol, acetonitrile, dioxane, isopropyl alcohol, and mixtures thereof.

In one embodiment, the process of the second aspect is conducted in the presence of an organic solvent selected from methyl tetrahydrofuran, methanol, acetonitrile, isopropyl alcohol, and mixtures thereof.

In one embodiment, the process of the second aspect is conducted in the presence of an organic solvent selected from tetrahydrofuran (THF), 2-methyltetrahydrofuran (2-MeTHF), methanol (MeOH), and mixtures thereof. Included in this embodiment is the process of the second aspect wherein said process is conducted in the presence of an organic solvent mixture of tetrahydrofuran, 2-methyltetrahydrofuran, and methanol. Suitable organic solvent mixtures include a mixture of about 4.5 to about 6.5 L/kg 2-MeTHF, about 2 to about 3 L/kg THF, and about 1.5 to about 2.5 L/kg MeOH; a mixture of about 5 to about 6 L/kg 2-MeTHF, about 2.2 to about 2.8 L/kg THF, and about 2.4 to about 2.6 L/kg MeOH; and a mixture of about 5.5 to about 5.8 L/kg 2-MeTHF, about 2.4 to about 2.6 L/kg THF, and about 1.9 to about 2.1 L/kg MeOH; based on Compound 5.

The process of the second aspect is conducted in the presence of water. Suitable amounts of water include from about 5 to about 7 L/Kg, from about 5.5 to about 6.5 L/Kg, and from 5.8 to about 6.2 L/Kg, based on Compound 5.

In one embodiment, the process of the second aspect is conducted in the presence of (i) a catalyst selected from palladium(II) acetate; (ii) a ligand selected from (R)-(+)-2,2'-bis(di-p-tolylphosphino)-1,1'-binaphthyl, (R)-(+)-2,2'-bis[di(3,5-xylyl)phosphino]-1,1'-binaphthyl, (R)-(+)-2,2'-bis(diphenylphosphino)-1,1'-binaphthyl, and (2'-(diphenylphosphino)-[1,1'-binaphthalen]-2-yl)diphenylphosphine oxide; (iii) a base selected from $K_3PO_4$; (iv) a solvent selected from tetrahydrofuran, 2-methyltetrahydrofuran, methanol, and mixtures thereof; and water.

In the process of the second aspect, suitable amounts of Intermediate B1 include from about 1.07 to about 1.25 equivalents, form about 1.1 to about 1.2 equivalents, and from about 1.12 to about 1.18 equivalents, based on equivalents of Compound 5.

In one embodiment, the process of the second aspect is conducted at a temperature in the range of about 0° C. to about 10° C. Other temperature ranges for the process of the second aspect include from about 4° C. to about 8° C., and from about 6° C. to about 8° C.

In one embodiment, the process of the second aspect provides an enriched mixture having a selectivity yield of at least 60%, 65%, 70%, 75%, 80%, 85%, 90%, or 95% for Compound 6 compared to its diastereomer.

In one embodiment, the process of the second aspect provides an enriched mixture having a selectivity ratio of at least 3:2, 2:1, 7:3, 3:1, 4:1, 5:1, 9:1, 10:1, 12:1, 15:1, 16:1, and 19:1 for Compound 6 compared to its diastereomer.

Compound 6 can be isolated and/or purified by various methods known in the art. Suitable methods include crystallization, chromatography, filtration, and distillation. Compound 6 can be isolated as a salt.

In the process of the second aspect, the activated catalyst is prepared by combining the catalyst with the ligand. Suitable temperatures include temperatures in the range of from about 62° C. to about 78° C., temperatures in the range of from about 65° C. to about 75° C., and temperatures in the range of from about 68° C. to about 72° C.

The process of the second aspect including the preparation of the activated catalyst can be conducted in the presence of oxygen levels in the range of from about 0 to about 1000 ppm, from about 0 to about 800 ppm, and from about 0 to about 400 ppm.

The third aspect of the invention is an amide coupling reaction. The process provides Compound 7 by forming an amide linkage between the amine group attached to the phenyl group of Compound 6 and the carboxylic acid group attached to Intermediate C3.

The process of the third aspect is conducted in the presence of a synthesis adjuvant selected from O-(benzotriazol-1-yl)-N,N,N',N'-tetramethyluronium tetrafluoroborate (TBTU), 1-[bis(dimethylamino)methylene]-1H-1,2,3-triazolo[4,5-b]pyridinium 3-oxide hexafluorophosphate (HATU), 1-ethyl-3-(3-dimethylaminopropyl) carbodiimide (EDAC), 2-hydroxypyridine-N-oxide (HOPO), and mixtures thereof.

In one embodiment, the process of the third aspect is conducted in the presence of a synthesis adjuvant selected from TBTU, HATU, EDAC, and mixtures thereof.

In one embodiment, the process of the third aspect is conducted in the presence of a synthesis adjuvant selected from TBTU.

In one embodiment, the process of the third aspect is conducted in the presence of a synthesis adjuvant selected from HATU.

In one embodiment, the reaction of the third aspect is conducted in the presence of a synthesis adjuvant selected from EDAC. Suitable amounts of EDAC include from about 1 to about 2 equivalents, from about 1.1 to about 1.7 equivalents, and from about 1.25 to about 1.55 equivalents, based on Compound 6.

The process of the third aspect is conducted in the presence of a base selected from DIPEA, 1-methylimidazole, 3,4-lutidine, pyridine, 4-picoline, 2,6-lutidine, dimethylaminopyridine (DMAP), N-methylmorpholine, tributyl amine, N-methylpyrrolidine, and mixtures thereof.

In one embodiment, the process of the third aspect is conducted in the presence of a base selected from DIPEA, 1-methylimidazole, 3,4-lutidine, and mixtures thereof. Included in this embodiment is the process of the third aspect wherein said process is conducted in the presence of a base selected from DIPEA, 1-methylimidazole, and 3,4-lutidine.

In one embodiment, the process of the third aspect is conducted in the presence of a base selected from DIPEA.

In one embodiment, the process of the third aspect is conducted in the presence of a base selected from 1-methylimidazole. Suitable amounts of base include from about 1 to about 2 equivalents of 1-methylimidazole, from about 1 to about 1.6 equivalents of 1-methylimidazole, and from about 1.15 to about 1.45 equivalents of 1-methylimidazole, based on Compound 6.

In one embodiment, the process of the third aspect is conducted in the presence of a base selected from 3,4-lutidine.

The process of the third aspect is conducted in the presence of an acid selected from methanesulfonic acid, ethanesulfonic acid, toluenesulfonic acid, hydrochloric acid, and mixtures thereof.

In one embodiment, the process of the third aspect is conducted in the presence of an acid selected from methanesulfonic acid, ethanesulfonic acid, toluenesulfonic acid, hydrochloric acid.

In one embodiment, the process of the third aspect is conducted in the presence of an acid selected from methanesulfonic acid. Suitable amounts of acid include about 0.3 to about 1 equivalent, about 0.4 to about 0.7 equivalents, and from 0.45 to about 0.55 equivalents of methanesulfonic acid, based on Compound 6.

In one embodiment, the process of the third aspect is conducted in the presence of an acid selected from ethanesulfonic acid.

In one embodiment, the process of the third aspect is conducted in the presence of an acid selected from toluenesulfonic acid.

In one embodiment, the process of the third aspect is conducted in the presence of an acid selected from hydrochloric acid.

In one embodiment, the process of the third aspect is conducted in the presence of a solvent selected from DMF, NMP, DMAc, and mixtures thereof. Included in this embodiment is the process of the third aspect, wherein said process is conducted in the presence of a solvent selected from DMF, NMP, and DMAc.

In one embodiment, the process of the third aspect is conducted in the presence of a solvent selected from DMF. Suitable amounts of solvent include from about 4 to about 20 L/kg DMF, from about 5 to about 10 L/kg DMF, and from about 6 to about 8 L/kg DMF, based on Compound 6.

In one embodiment, the process of the third aspect is conducted in the presence of a solvent selected from NMP.

In one embodiment, the process of the third aspect is conducted in the presence of a solvent selected from DMAc.

In one embodiment, the process of the third aspect is conducted at a temperature in the range of about 0° C. to about 50° C. Suitable temperature ranges for the process of the third aspect include about 0° C. to about 30° C.; about 0° C. to about 20° C.; about 0° C. to about 25° C.; about 5° C. to about 30° C.; about 5° C. to about 20° C.; and about 5° C. to about 15° C.

In one embodiment, the process of the third aspect is conducted in the presence of:
(i) an adjuvant selected from TBTU, HATU, EDAC, HOPO, and mixtures thereof;
(ii) a base selected from DIPEA, 1-methylimidazole, 3,4-lutidine, and mixtures thereof;
(iii) an acid selected from methanesulfonic acid, ethanesulfonic acid, toluenesulfonic acid, hydrochloric acid, and mixtures thereof; and
(iv) a solvent selected from DMF, NMP, DMAc, and mixtures thereof; at a temperature in the range of from about zero to about 30° C.

In one embodiment, the process of the third aspect is conducted in the presence of:
(i) an adjuvant selected from TBTU, HATU, EDAC, and mixtures thereof; and
(ii) a base selected from DIPEA, 1-methylimidazole, 3,4-lutidine, and mixtures thereof;
(iii) an acid selected from methanesulfonic acid, ethanesulfonic acid, toluenesulfonic acid, hydrochloric acid, and mixtures thereof; and
(iv) a solvent selected from DMF, NMP, DMAc, and mixtures thereof; at a temperature in the range of from zero to 20° C. Included in this embodiment is the process of the third aspect wherein said process is conducted in the presence of a base selected from DIPEA, 1-methylimidazole, and 3,4-lutidine.

In one embodiment, the process of the third aspect is conducted in the presence of:
(i) an adjuvant selected from TBTU, HATU, EDAC, and mixtures thereof;
(ii) a base selected from 1-methylimidazole;
(iii) an acid selected from methanesulfonic acid, ethanesulfonic acid, and mixtures thereof; and
(iv) a solvent selected from DMF, NMP, DMAc, and mixtures thereof;
at a temperature in the range of from zero to 20° C.

In embodiment, the process of the third aspect provides a process for the preparation of Compound 7 from Compound 6 and Intermediate C3 wherein R is $C_2$-$C_4$ alkyl. Included in this embodiment is a process in which Compound 7 is prepared from a Compound 6 and Intermediate C3 wherein R is ethyl, n-propyl, or n-butyl. Also included is a process in which Compound 7 is prepared from Compound 6 and Intermediate C3 wherein R is n-propyl.

In the process of the third aspect, suitable amounts of Intermediate C3 include from about 1 to about 2 equivalents, from about 1.05 to about 1.5 equivalents, and from about 1.1 to about 1.3 equivalents, based on equivalents of Compound 6.

Compound 7 can be isolated and/or purified by various methods known in the art. Suitable methods include crystallization, chromatography, filtration, and distillation.

One embodiment provide Intermediate C3 or a salt thereof, wherein R is $C_{1-4}$ alkyl.

One embodiment provide Intermediate C3 or a salt thereof, wherein R is $C_{2-4}$ alkyl.

One embodiment provide Intermediate C3 or a salt thereof, wherein R is ethyl, n-propyl, or n-butyl.

One embodiment provide Intermediate C3 or a salt thereof, wherein R is n-propyl.

The present invention may be embodied in other specific forms without departing from the spirit or essential attributes thereof. This invention encompasses all combinations of the aspects and/or embodiments of the invention noted herein. It is understood that any and all embodiments of the present invention may be taken in conjunction with any other embodiment or embodiments to describe additional embodiments. It is also to be understood that each individual element of the embodiments is meant to be combined with any and all other elements from any embodiment to describe an additional embodiment.

Definitions

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof. Embodiments identified herein as exemplary or preferred are intended to be illustrative and not limiting.

Unless specifically stated otherwise herein, references made in the singular may also include the plural. For example, "a" and "an" may refer to either one, or one or more.

As used herein, the phase "compound and/or salts thereof" refers to a compound, at least one salt of the compound, or a combination thereof. For example, a compound and/or salts thereof includes a compound; a salt of a compound; a compound and one or more salts of the compound; and two or more salts of a compound.

Unless otherwise indicated, any atom with unsatisfied valences is assumed to have hydrogen atoms sufficient to satisfy the valences.

The definitions set forth herein take precedence over definitions set forth in any patent, patent application, and/or patent application publication incorporated herein by reference.

Listed below are definitions of various terms used to describe the present invention. These definitions apply to the terms as they are used throughout the specification (unless they are otherwise limited in specific instances) either individually or as part of a larger group.

Throughout the specification, groups and substituents thereof may be chosen by one skilled in the field to provide stable moieties and compounds.

In accordance with a convention used in the art,

is used in structural formulas herein to depict the bond that is the point of attachment of the moiety or substituent to the core or backbone structure.

The term "alkyl" as used herein, refers to both branched and straight-chain saturated aliphatic hydrocarbon groups containing, for example, from 1 to 12 carbon atoms, from 1 to 6 carbon atoms, and from 1 to 4 carbon atoms. Examples of alkyl groups include, but are not limited to, methyl (Me), ethyl (Et), propyl (e.g., n-propyl and i-propyl), butyl (e.g., n-butyl, i-butyl, sec-butyl, and t-butyl), and pentyl (e.g., n-pentyl, isopentyl, neopentyl), n-hexyl, 2-methylpentyl, 2-ethylbutyl, 3-methylpentyl, and 4-methylpentyl. When numbers appear in a subscript after the symbol "C", the subscript defines with more specificity the number of carbon atoms that a particular group may contain. For example, "$C_{1-3}$ alkyl" denotes straight and branched chain alkyl groups with one to three carbon atoms.

The term "benzyl," as used herein, refers to a methyl group in which one of the hydrogen atoms is replaced by a phenyl group.

The compounds can form acid salts which are also within the scope of this invention. Unless otherwise indicated, reference to an inventive compound is understood to include reference to one or more salts thereof. The term "salt(s)" denotes acidic salts formed with inorganic and/or organic acids. Pharmaceutically acceptable (i.e., non-toxic, physiologically acceptable) salts are preferred. However, other salts may be useful, e.g., in isolation or purification steps which may be employed during preparation, and thus, are contemplated within the scope of the invention. Salts of the compounds may be formed, for example, by reacting a compound with an amount of acid, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, maleates (formed with maleic acid), 2-hydroxyethanesulfonates, lactates, methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Compound 2, Compound 3, Compound 4, Compound 5, Compound 6, Intermediate A1, Intermediate A2, Intermediate B1, Intermediate C2, and Intermediate C3 can be isolated as salts.

It should further be understood that solvates (e.g., hydrates) of the compounds are also within the scope of the present invention. The term "solvate" means a physical association of a compound with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, isopropanolates, acetonitrile solvates, and ethyl acetate solvates. Methods of solvation are known in the art.

In addition, Compound 1, Compound 2, Compound 3, Compound 4, Compound 5, Compound 6, Compound 7, and Compound 8, subsequent to their preparation, can be isolated and purified to obtain a composition containing an amount by weight equal to or greater than 99% of a compound of Compound 1, Compound 2, Compound 3, Compound 4, Compound 5, Compound 6, Compound 7, and Compound 8 ("substantially pure"), respectively, which is then used or formulated as described herein. Such "substantially pure" Compound 1, Compound 2, Compound 3, Compound 4, Compound 5, Compound 6, Compound 7, and Compound 8 are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

The compounds of the present invention are intended to include all isotopes of atoms occurring in the present compounds. Isotopes include those atoms having the same atomic number but different mass numbers. By way of general example and without limitation, isotopes of hydrogen include deuterium (D) and tritium (T). Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. For example, methyl (—$CH_3$) also includes deuterated methyl groups such as —$CD_3$.

EXAMPLES

The invention is further defined in the following Example. It should be understood that the Example is given by way of illustration only. From the above discussion and the Example, one skilled in the art can ascertain the essential characteristics of the invention, and without departing from the spirit and scope thereof, can make various changes and modifications to adapt the invention to various uses and conditions. As a result, the invention is not limited by the illustrative examples set forth hereinbelow, but rather is defined by the claims appended hereto.

Abbreviations

S-(+) DTBM-SEGPHOS (S)-(+)-5,5'-bis[di(3,5-di-tert-butyl-4-methoxyphenyl) phosphino]-4,4'-bi-1,3-benzodioxole
[Rh(cod)Cl]$_2$ bis(1,5-cyclooctadiene)dirhodium(I) dichloride
DIPEA N,N-diisopropylethylamine
GCAP Gas chromatography area percent
RT retention time
Pd(OAc)$_2$ palladium(II) acetate
P(o-tolyl)$_3$ tri(o-tolyl)phosphine
MeOH methanol
KOAc potassium acetate
(R)-BINAP (R)-(+)-2,2'-bis(diphenylphosphino)-1,1'-binaphthyl
THF tetrahydrofuran
MeTHF 2-methyltetrahydrofuran
n-BuOH n-butyl alcohol
Pt/C platinum/carbon
DMSO dimethyl sulfoxide
TFA trifluoroacetate
DMF dimethylformamide
MTBE methyl t-butyl ether Intermediate A1

2-amino-4-bromo-5-fluorobenzoic acid

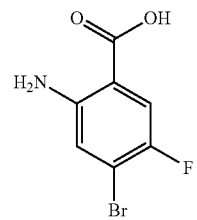

(A1)

5% Pt/C (50% water-wet) (60 g, 6 wt %) was charged to a nitrogen blanketed vessel containing isopropyl acetate (22 L) and 4-bromo-5-fluoro-2-nitrobenzoic acid (1.00 kg, 3.79 mol). The headspace was exchanged three times with nitrogen and followed three times with hydrogen. The reaction mixture was stirred at 25° C. under an atmosphere of hydrogen. After 40 hours, the reaction was complete and the headspace was exchanged three times with nitrogen. The reaction mixture was filtered. The reaction vessel and filter train were rinsed with isopropyl acetate (5 L). The combined organic layers were concentrated under reduced pressure to 5.0 L. The solvent was then exchanged to toluene under reduced pressure and the resulting solids were isolated by filtration, washed with toluene, and dried at 50° C. under reduced pressure to afford 0.59 kg (66% yield) of 2-amino-4-bromo-5-fluorobenzoic acid as a white to off-white crystalline solid.

Additional 2-amino-4-bromo-5-fluorobenzoic acid was obtained by washing the spent catalyst twelve times with 2.75:1 w/w THF in water (9.0 L). Each portion of wash was allowed to soak the spent catalyst for 30 minutes. The filtrate was concentrated to 10 L. The resulting solids were isolated by filtration, washed with water (1.0 L), and dried at 40° C. under reduced pressure to afford 0.15 kg (17% yield) of 2-amino-4-bromo-5-fluorobenzoic acid as an off-white crystalline solid. $^1$H NMR (400 MHz, DMSO-d$_6$) δ8.74 (br s, 2H), 7.50 (d, J=9.6 Hz, 1H), 7.08 (d, J=6.1 Hz, 1H). $^{13}$C NMR (101 MHz, DMSO-d$_6$) δ168.2, 149.5, 148.8, 147.2, 119.9, 117.0, 116.8, 114.8, 114.6, 109.1. HPLC Conditions: Column: Waters X-bridge C-18 (150×4.6 mm, 3.5µ; Column Temeprature: 30° C.; Solvent A: 0.05% TFA in water:acetonitrile (95:05 v/v); Solvent B: 0.05% TFA in water:acetonitrile:methanol (05:75:20 v/v); Diluent: 0.25 mg/ml in acetonitrile; Gradient: % B: 0 min. 5%; 20 min. 95%; 25 min. 95%; 26 min. 5%; stop time 30 min; Flow Rate: 0.8 ml/min; Wavelength: 230 nm; The retention time of 2-amino-4-bromo-5-fluorobenzoic acid was 13.2 min. The retention time of 4-bromo-5-fluoro-2-nitrobenzoic acid was 12.9 min.

Intermediate A2

4-bromo-5-fluoro-2-hydrazinylbenzoic acid hydrochloride

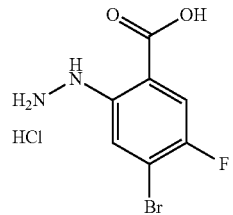

(A2)

A solution of sodium nitrite (100.0 g, 6.38 mol) and water (1.8 L) was slowly charged to a cold slurry (0° C.) of 2-amino-4-bromo-5-fluorobenzoic acid (1.00 kg, 4.27 mol) in water (2.2 L) containing 35% HCl (2.1 kg, 20.15 mol). The reaction mixture slurry was stirred at 0° C. for 5 hours. The resultant cold diazonium salt slurry was charged over 4 hours to a cold solution (0° C.) of sodium bisulfite (2.66 kg, 25.0 mol in water (7.5 L). The diazonium reaction vessel was rinsed with cold water (2.5 L). The rinse water was transferred slowly to the reaction mixture. After 40 minutes, the reaction mixture was warmed to 20° C. over one hour. The reaction mixture slurry was stirred at 20° C. for 3 hours. After 3 hours, the reaction mixture was slowly transferred to a 60° C. solution of 35% HCl (15.0 kg, 144.0 mol) and water (3.0 L). The vessel was rinsed with water (2.5 L); and transferred to 35% HCl and water reaction mixture. The reaction mixture was stirred at 60° C. for 2 hours. The product was isolated by filtration and washed with water (3.0 L). The wet cake was charged back to the reactor and was slurried with isopropyl acetate (9.0 L) for 1 hour at 20° C. The product was isolated by filtration, washed with isopropyl acetate (1.0 L), and dried at 45-50° C. under reduced pressure to afford 0.99 kg (81% yield) of 4-bromo-5-fluoro-2-hydrazinylbenzoic acid hydrochloride as an off-white crystalline solid in 95% purity. $^1$H NMR (400 MHz, DMSO-d$_6$) δ10.04 (br s, 3H), 9.00 (br s, 1H), 7.74 (d, J=9.1 Hz, 1H), 7.61 (d, J=5.8 Hz, 1H). $^{13}$C NMR (101 MHz, DMSO-d$_6$) δ167.3, 153.0, 150.6, 144.5, 119.2, 118.0, 114.6. HPLC analysis: Column: Zorbax Eclipse Plus C18 3.5 um, 150×4.6 mm ID; Column Temeprature: 30° C.; Solvent A: 10 mM ammonium formate in water:MeOH (90:10 v/v); Solvent B:MeOH:ACN (70:30 v/v); Diluent: 50% CH$_3$CN(aq); Gradient: % B: 0 min. 0%; 15 min. 90%; 18 min. 100%; stop time 18 min; Flow Rate: 1.0 ml/min; Wavelength: 240 nm. The retention time of the diazonium salt intermediate was 3.7 min. The retention time of the mono-sulfamic acid intermediate was 5.2 min. The retention time of 4-bromo-5-fluoro-2-hydrazinylbenzoic acid hydrochloride was 8.0 min. The retention time of 2-amino-4-bromo-5-fluorobenzoic acid was 8.7 min.

Intermediate B1

(3-amino-2-methylphenyl)boronic acid hydrochloride

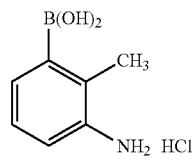

(B1)

A 500 mL ChemGlass reactor (Reactor A) was equipped with mechanical stirrer and a nitrogen inlet. To the reactor was added 150 ml of methyl tetrahydrofuran. Next, Pd(OAc)$_2$ (241 mg, 0.02 eq) was added, followed by the addition of P(o-tolyl)$_3$ ligand (654 mg, 0.04 eq). The containers holding the Pd(OAc)$_2$ and P(o-tolyl)$_3$ were rinsed with 15 ml of methyl tetrahydrofuran, and the rinse solvents were added to the reactor. The reactor was sealed, evacuated to less than 150 mbar, and filled with nitrogen gas. This was repeated an additional four times to reduce the oxygen level to below 400 ppm. The reaction mixture was stirred for 30 min. Next, 10 g (1.0 eq) of 3-bromo-2-methyl aniline was charged to the inerted reactor. The container that held the 3-bromo-2-methyl aniline was rinsed with 15 ml of Me-THF and added into the reactor. KOAc (15.6 g, 3 eq) was added to the reactor. A slurry formed. The reaction mixture was inerted by using three vacuum/nitrogen cycles to an oxygen endpoint of less than 400 ppm.

A second 500 ml ChemGlass reactor was charged with 150 mL of MeOH, followed by the addition of 7.2 g (1.5 eq) of B$_2$(OH)$_4$. The resultant slurry was agitated at 25° C. After 30 min, the B$_2$(OH)$_4$ was fully dissolved. The homogeneous solution was inerted by using 5 vacuum/nitrogen purge cycles to reduce the oxygen level to less than 400 ppm. The B$_2$(OH)$_4$/MeOH solution was transferred to Reactor A under a nitrogen atmosphere.

The reactor was inerted using three vacuum/nitrogen cycles with agitation to reduce the oxygen level to less than 400 ppm. The batch was heated to 50° C. (internal batch temperature). A slurry was observed when the temperature reached 40° C. After reacting for 3 hrs, HPLC analysis of the reaction mixture showed 0.2 AP starting material remained. N-acetyl cysteine (2.0 g, 0.2 g/g) was added to Reactor A. The reaction mixture was stirred at 50° C. (internal batch temperature) for 30 min. The reaction stream was concentrated through distillation to 5 ml/g (~50 ml). Methyl tetrahydrofuran (200 ml, 20 ml/g) was charged to the slurry. The slurry was then concentrated via distillation to 150 ml (15 ml/g). Methyl tetrahydrofuran (150 ml, 15 ml/g) was charged to the reaction mixture. The slurry was cooled to 20° C. (batch temperature). Brine (26 wt %, 25 ml, 2.5 ml/g) was charged followed by the addition of aqueous Na$_2$CO$_3$ (20 wt %, 15 ml, 1.5 ml/g). The reaction mass was agitated at a moderate rate (50~75/min) for 30 min. Celite (1 g, 0.1 g/g) was charged to the bi-phasic solution. The resultant slurry was agitated for 30 min. The slurry was filtered and transferred to Reactor B. The Celite cake was washed with 10 ml of methyl tetrahydrofuran. The bottom, lean aqueous phase was split from the organic phase and discarded. Brine (26 wt %, 25 ml, 2.5 ml/g) was charged followed by the addition of aqueous Na$_2$CO$_3$ (20 wt %, 15 ml, 1.5 ml/g) to the organic solution. The resultant bi-phasic solution was agitated at a moderate rate (75 rpm) for 30 min. The bottom, lean aqueous phase was split from the organic phase and discarded. B$_2$(OH)$_4$ analysis of the rich organic solution did not detect B$_2$(OH)$_4$.

In Reactor B, the rich organic phase was concentrated via distillation to 50 ml (5 ml/g). The concentrated solution was cooled to 0-5° C. (batch temp). Concentrated HCl (1.06 kg, 2.0 eq) was charged to the solution over 30 min with the batch temperature maintained below 10° C. Once the concentrated HCl was added, a slurry formed. The slurry was agitated for 2 h at 5° C. The slurry was filtered. The wet cake was washed with methyl tetrahydrofuran (2×20 ml). The cake was collected and dried at 50° C. under 100 mbar vacuum for 6 h to afford 8.4 g of 3-amino-2-methylphenyl)boronic acid hydrochloride as a white solid (83.5% yield). $^1$H NMR (500 MHz, D$_2$O) δ 7.48-7.23 (m, 3H), 4.78 (br s, 5H); 2.32 (s, 3H). $^{13}$C NMR (126 MHz, D$_2$O) δ 135.2, 134.7, 130.1, 128.0, 124.3, 17.4.

HPLC analysis: Column: Zorbax Eclipse Plus C18 3.5 um, 150×4.6 mm ID; Solvent A: 10 mM ammonium formate in water:MeOH=90:10); Solvent B: CH$_3$CN:MeOH (30:70 v/v); Gradient: % B: 0 Min. 0%; 1 Min. 0%; 15 Min. 90%; 15.1 Min. 0%; Stop Time: 20 min; Flow Rate: 1 ml/min; wavelength: 240 nm. The retention time of (3-amino-2-methylphenyl)boronic acid hydrochloride was 4.4 min. The retention time of (3-amino-2-methylphenyl)boronic acid hydrochloride was 17.8 min.

Intermediate C1

7-fluoro-1-methylindoline-2,3-dione

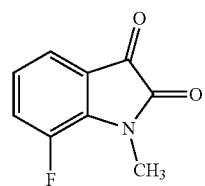

(C1)

N,N-dimethylformamide (540.0 mL, 6980 mmol, 100 mass %) was added to a 2-L ChemGlass reactor equipped with a mechanical agitator, a temperature probe, and a cooling/heating circulator. Next, 7-fluoroindoline-2,3-dione (135.0 g, 817.6 mmol, 100 mass %) was added at 25° C. and dissolved to form a dark red solution. The charging ports and the beaker that contained the 7-fluoroindoline-2,3-dione were washed with N,N-dimethylformamide (135.0 mL, 1750 mmol, 100 mass %) and the rinse solution was poured into the reactor. Next, cesium carbonate 60-80 mesh (203.66 g, 625.05 mmol, 100 mass %) was added portion-wise to the reaction mixture. The addition was exothermic and the temperature of the reaction mixture increased from 20 to 25.5° C. The color of the reaction mixture changed from a dark red solution to a black solution. The reactor jacket temperature was set to 0° C. Next, iodomethane (56.5 mL, 907 mmol, 100 mass %) was added slowly via an additional funnel at ambient temperature, (iodomethane temperature) while maintaining the batch temperature at less than 30° C. Upon stirring, the reaction was exothermic, reaching a temperature of 29.3° C. The batch temperature decreased to 26.3° C. after 85% of iodomethane was added, and the reaction mixture turned from black to an orange. After the addition of the iodomethane was completed, the jacket temperature was raised to 25.5° C. The reaction mixture was stirred at 25° C. for 2 hrs.

The reddish orange-colored reaction mixture was transferred to a 1 L Erlenmeyer flask. The reaction mixture was filtered through a ceramic Buchner funnel with a No. 1 Whatman filter paper to remove solid $Cs_2CO_3$ and other solid by-products. In addition to a light-colored powder, there were yellow to brown colored rod-shaped crystals on top of the cake, which were water soluble. The filtrate was collected in a 2-L Erlenmeyer flask. The solids cake was washed with N,N-dimethylformamide (100.0 mL, 1290 mmol, 100 mass %). The DMF filtrate was collected in a 2-L Erlenmeyer flask.

To a separate 5-L ChemGlass reactor was charged water (3000.0 mL, 166530 mmol, 100 mass %). Next, 1.66 g of 7-fluoro-1-methylindoline-2,3-dione was added as seed to the water to form an orange colored suspension. The DMF filtrate was charged to the 5-L reactor slowly while maintaining the batch temp. at less than 29° C. over a period of 60 min. Stirring was maintained at 290 rpm. The orange solids precipitated instantly. The 2-L Erlenmeyer flask was rinsed with N,N-dimethylformamide (55.0 mL, 711 mmol, 100 mass %) and charged to the 5-L reactor. The slurry was cooled to 25° C. and agitated at 200 rpm for 12 hrs. The mixture remained as a bright orange-colored suspension. The slurry was filtered over a No. 1 Whatman filter paper in a 9 cm diameter ceramic Buchner funnel to a 4 L Erlenmeyer flask to provide a bright orange-colored cake. The cake was washed with 1200 mL of water via rinsing the 5000 mL reactor (400 mL×2), followed by 300 mL of deionized water introduced directly on the orange cake. The wet cake was dried under suction for 40 min at ambient temperature until liquid was not observed to be dripping from the cake. The cake was introduced into a vacuum oven (800 mbar) with nitrogen sweeping at ambient temperature for 1 hr, at 40-45° C. for overnight, and at 25° C. for 1 day to provide 7-fluoro-1-methylindoline-2,3-dione (Q, 130.02 g, 725.76 mmol, 100 mass %, 88.77% yield) as a bright orange-colored solid. $^1$H NMR (400 MHz, DMSO-$d_6$) δ 7.57 (ddd, J=12.0, 8.5, 1.0 Hz, 1H), 7.40 (dd, J=7.3, 1.0 Hz, 1H), 7.12 (ddd, J=8.5, 7.5, 4.0 Hz, 1H), 3.29 (d, J=3.0 Hz, 3H). $^{13}$C NMR (101 MHz, DMSO-$d_6$) δ182.3, 158.2, 148.8, 146.4, 137.2, 125.9, 124.3, 120.6, 28.7.

Intermediate C2

3-fluoro-2-(methylamino)benzoic acid

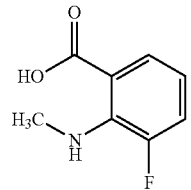

(C2)

To a 1-L three neck round bottom flask equipped with a mechanical overhead agitator, a thermocouple, and an ice-water bath was charged NaOH (5.0 N) in water (140.0 mL, 700 mmol, 5.0 mol/L) followed by deionized water (140.0 mL, 7771 mmol, 100 mass %) to form a colorless transparent solution (T=20.2° C.). 7-fluoro-1-methylindoline-2,3-dione (R, 25 g, 139.55 mmol, 100 mass %) was charged portion-wise while controlling the batch temperature at less than 24° C. with an ice-water bath to provide cooling. 7-fluoro-1-methylindoline-2,3-dione was charged and 50 mL of water was used to rinse off the charging funnel, the spatula, and the charging port. The reaction mixture was a thick yellow-green hazy suspension. The yellow-greenish suspension was cooled to 5.0° C. with an ice-water bath. The mixture was stirred for 15 min. Next, hydrogen peroxide (50% wt.) in water (11.0 mL, 179 mmol, 50 mass %) was charged to a 60 mL additional funnel with deionized (4.0 mL, 220 mmol, 100 mass %). The concentration of $H_2O_2$ post dilution was ~36.7%. The dilute hydrogen peroxide solution was added over a period of 11 minutes to the 1 L round bottom flask cooled with an ice-water bath and stirred at 350 rpm. The reaction mixture color was observed to become lighter in color and less viscous after 5 mL of the peroxide solution was added. After adding 10 mL of peroxide solution, the reaction mixture became clear with visible solids. At the end of addition, the reaction mixture was a green-tea colored transparent solution. The ice-water bath was removed (batch temperature was 16.6° C.), and the transparent, greenish yellow reaction mixture was allowed to warm to ambient temperature (21.0° C.), stirred for 1 hr.

After the reaction was complete, (1.0 hr), the reaction mixture was cooled to 4.3° C. with an ice-water bath. The reaction mixture was neutralized by the addition 6.0 N HCl (aq.) over a period of 3 hours to minimize foaming and the exotherm, resulting in the formation of a yellow-green suspension. The ice-bath was removed and the quenched reaction mixture was stirred at ambient temperature for 20 min. The yellow-green colored reaction mixture was transferred to a 2 L separatory funnel. Dichloromethane (300.0 mL, 4680 mmol, 100 mass %) was charged to the separatory funnel via rinsing the 1 L 3-necked round bottom flask. The separatory funnel was shaken vigorously, then allowed to settle (phase split was fast). Gas evolution was minor. The top aqueous layer was dark amber in color. The bottom dichloromethane layer was tea-green in color. The bottom rich dichloromethane layer was transferred to a clean 1 L Erlenmeyer flask. Next, the 1 L three necked round bottom flask was rinsed again with dichloromethane (200.0 mL, 3120 mmol, 100 mass %). The dichloromethane rinse was added to the separatory funnel. The separatory funnel was shaken vigorously and allowed to settle (phase split was fast). The top aqueous layer was amber in color (lighter); the bottom dichloromethane layer was lighter green. The bottom rich dichloromethane layer was transferred to the 1 L Erlenmeyer flask. Dichloromethane (200.0 mL, 3120 mmol, 100 mass %) was charged to the separatory funnel and the separatory funnel was shaken vigorously. The contents were allowed to settle (phase split was fast). The bottom rich dichloromethane layer was transferred to the same 1 L Erlenmeyer flask. Peroxide test strip showed >10 mg/Liter peroxide concentration. The total volume of the aqueous layer was 540 mL.

In a separate 250-mL Erlenmeyer flask was added sodium thiosulfate pentahydrate (20.0 g, 80.6 mmol, 100 mass %) followed by deionized water (180.0 mL, 9992 mmol, 100 mass %) to form a colorless solution (10% wt. solution). The sodium thiosulfate solution was added to the combined dichloromethane rich solution in the 1 L Erlenmeyer flask. The contents of the flask were stirred vigorously for 10 hrs at ambient temperature. Peroxide strip did not detect the presence of peroxides in the bottom DCM layer. The top Na$_2$S$_2$O$_3$ layer was amber in color, the bottom dichloromethane layer was much lighter in color, but was still amber in color. After 10 hrs, the mixture was transferred to a 1 L separatory funnel. The top aqueous layer was discarded.

The dichloromethane solution was washed with 150.0 mL of saturated brine solution. After phase split, the bottom rich dichloromethane layer was transferred to a 1 L flask. The dichloromethane solution was distilled to approximately 150 mL to obtain an amber-colored solution. Next, dichloromethane (120 mL, 1872 mmol, 100 mass %) was added and the mixture was heated to 35-40° C. to fully dissolve the solids. The amber solution was filtered through a 0.45 micron PTFE membrane Zap Cap filtration unit into a 1 L flask. The filtrate was transferred into a 3-neck 1 L round bottom flask fitted with a thermocouple, a heating mantle, a mechanical agitator, and a condenser with a nitrogen inlet. To the flask was charged dichloromethane (120 mL, 1872 mmol, 100 mass %) via rinsing the 1 L flask. The contents of the flask were concentrated under reduced pressure to approximately 140 mL to afford a yellow-green-colored suspension. The mixture was heated to 40.5° C. (refluxing) with stirring at 155 rpm to form a green-colored suspension with white solid pieces. After refluxing for 5 min, heptane (100.0 mL, 683 mmol, 100 mass %) was charged to the above mixture. The batch temperature dropped from 41.3° C. to 33.8° C. and the reaction mixture was a suspension. The mixture was heated to 45° C. The mixture remained as a suspension with supernatant being amber with white solids. The refluxing was mild. After 36 minutes, (batch temp.=43.8° C.), heptane (120.0 mL, 819 mmol, 100 mass %) was added to the mixture. The batch temperature dropped to 38.0° C. The reaction mixture was a suspension. The mixture was heated to 40-45° C. and seeded with 0.3 g of 3-fluoro-2-(methylamino)benzoic acid. The reaction mixture remained as a suspension with supernatant being amber and solid pieces of white color. At t=1 h 25 min (T=45.4° C.) heptane (100.0 mL, 683 mmol, 100 mass %) was charged to the mixture causing the temperature to drop to 41.0° C. At t=2 h 13 min, (T=45.6° C.) additional heptane (100.0 mL, 683 mmol, 100 mass %) was added to the mixture causing temperature to drop to 41.7° C. At t=3 h 07 min, (T=45.5° C.), the heating was stopped. The mixture was allowed to cool to 20-25° C. under a nitrogen blanket. The suspension was agitated at ambient temperature for 12 hrs. The mixture was filtered using No. 1 Whatman filter paper fitted in a ceramic Buchner funnel to a 1 L Erlenmeyer flask. The solids were observed to settle quickly. The mother liquor was green in color. The bottom half of the round bottom flask was coated with a thin dark amber or brown film, which was water soluble. The 1 L round bottom flask was washed with 150 mL of heptane, and then the heptane was used to wash the collected off-white-colored solid.

The filter cake was allowed to dry at ambient temperature with suction for 10 min., then dried in a vacuum oven with nitrogen sweeping at 45-50° C. for 4 hrs, followed by drying at ambient temperature for 10 hrs, with nitrogen sweeping. 3-fluoro-2-(methylamino)benzoic acid (16.1 g) was isolated in 68.1% yield. $^1$H NMR (400 MHz, DMSO-d$_6$) δ7.61 (d, J=7.7 Hz, 1H), 7.23 (dq, J=7.9, 1.6 Hz, 1H), 6.57 (td, J=8.0, 4.4 Hz, 1H), 3.02 (d, J=6.8 Hz, 4H). $^{13}$C NMR (101 MHz, DMSO-d$_6$) δ 169.5, 153.1, 150.7, 141.8, 141.7, 127.4, 127.4, 120.9, 120.7, 114.8, 114.7, 114.4, 114.3, 32.8.

Intermediate C3

3-fluoro-2-(methyl(propoxycarbonyl)amino)benzoic acid

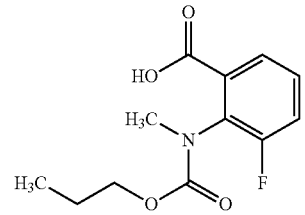

(C3)

A 20 L jacketed glass reactor with an overhead mechanical agitator, a thermocouple, a nitrogen inlet, a glass baffle, and a condenser rinsed with 4 liters of dichloromethane followed by nitrogen sweeping through bottom valve overnight. To the reactor was charged 3-fluoro-2-(methylamino)benzoic acid (1004.7 g, 5939.7 mmol, 100 mass %) followed by dichloromethane (6000 mL, 93400 mmol, 99.8 mass %) to form an off-white-colored suspension. Next, cesium carbonate (1035.2 g, 3170 mmol, 99.9 mass %) was added followed the addition of water (6000 g, 333056 mmol, 99 mass %) at ambient temperature. The batch temperature rose from 17.0° C. to 29.6° C. prior to addition of the water. Gas evolution was observed during the water charging. The colorless biphasic mixture was stirred for 15 min. The batch temperature was approximately 18.8° C. Next, n-propyl chloroformate (806.0 g, 6445.4 mmol, 98 mass %) was charged to an addition funnel. The reaction mixture was cooled to 15.0° C. with a glycol circulator. The n-propyl chloroformate was added from the addition funnel to the mixture while maintaining the batch temperature between 15.0 and 20.0° C. over 1 hr with stirring at 156 rpm. At the end of the addition, the batch temperature was 18.1° C. The jacket temperature was increased to 20° C. The white milky reaction mixture was agitated for 90 minutes.

The agitation was stopped and the reaction mixture was allowed to settle for phase split for 50 min. The hazy, bottom rich dichloromethane layer split from the aqueous layer and was transferred to a carboy. Next, 500 g of anhydrous Na$_2$SO$_4$ (s) and 100 g of 60-200 mesh silica gel was added to the dichloromethane solution of 3-fluoro-2-(methyl(propoxycarbonyl)amino)benzoic acid in the carboy. The dichloromethane solution was allowed to dry overnight.

The dichloromethane solution containing the 3-fluoro-2-(methyl (propoxycarbonyl)amino)benzoic acid was transferred from the carboy to a clean 20 L reactor via a 10 micron Cuno® in-line filter under vacuum to remove solid Na$_2$SO$_4$ and silica gel. The carboy was rinsed with 1 liter×2 of dichloromethane to remove residual solids. The dichloromethane was distilled off in the 20 L reactor with the jacket temperature set at 32° C., the batch temperature at 15° C., and vacuum set to 200-253 torr. At the end of distillation, the crude product was a thick light-amber-colored syrup. The solution was concentrated to 3 L of dichloromethane, and refilled with 3 L of dichloromethane each time to a final fill volume of 6 L. Next, 1 liter of dichloromethane was charged via vacuum to the residue in the 20-L reactor. The solution of 3-fluoro-2-(methyl(propoxycarbonyl)amino) benzoic acid became hazier. The solution was filtered using a Buchner funnel with a No. 1 filter paper into a new carboy. The reactor was rinsed with 500 mL×2 of dichloromethane and the rinse was filtered through the same Buchner funnel. All the filtrates were combined in a carboy and stored at the ambient temperature under nitrogen. Yellow-colored solids were observed to settle at the bottom of the carboy. The solution of 3-fluoro-2-(methyl (propoxycarbonyl)amino) benzoic acid in dichloromethane was transferred back to the clean 20-L reactor via vacuum and a 1 micron Cuno® in-line filter. The filtrate was still slightly hazy. The carboy was rinsed with 300 mL×3 of dichloromethane and the rinses were transferred to the reactor via the 1 micron Cuno® filter. The reactor walls were rinsed with 500-mL of dichloromethane. The dichloromethane solution was concentrated by distillation under reduced pressure until the volume was less than 2.0 liters.

The temperature of the reactor jacket was lowered to 30° C. The vacuum was broken and the reactor was filed with nitrogen. To the reactor was added 2 liters of cyclohexane followed by 5.0 g of 3-fluoro-2-(methyl(propoxycarbonyl) amino)benzoic acid crystalline seed. The seeds did not dissolve. The mixture was allowed to stir at 30° C. for 5-10 min to form a thick slurry. Additional cyclohexane (2.0 L) was added over 2 minutes. The jacket temperature was lowered to 25° C. The mixture was allowed to stir for 40 min. Additional cyclohexane (2.0 L) was added over 2 minutes. The jacket temperature was lowered to 23° C. The suspension was maintained at 23° C. for 60 min. Additional cyclohexane (2.0 L) was added over 2 minutes. The suspension was stirred for 20 min. The jacket temperature was lowered to 19.0° C. The suspension was maintained at 19-21° C. for 10 hrs. The slurry settled well after overnight aging. A sample of the supernatant was obtained and assessed for the loss based on 9.5 L total volume. The slurry was filtered to collect solids via a ceramic Buchner funnel with a No. 1 Whatman filter paper. The solids were crystalline and white when dry. The wet cake was washed with cyclohexane (~2000 mL×3) followed by drying for 10 min. The cake volume was 4933 cm³. The wet cake was transferred to four Pyrex glass trays for heated drying. The drying was continued in a vacuum oven at ×35-40° C. with nitrogen sweeping for 12 hrs to afford 1302.9 g of 3-fluoro-2-(methyl (propoxycarbonyl)amino) benzoic acid in 85.9% yield. $^1$H NMR (400 MHz, DMSO-$d_6$) (3:1 mixture of rotamers) δ 13.2 (br s, 1H), 7.72-7.67 (m, 1H), 7.58-7.52 (m, 1H), 7.49-7.43 (m, 1H), 4.06-3.95 (m, 0.50H), 3.90-3.80 (m, 1.50H) 3.12 (s 0.75H), 3.12 (s 2.25H), 1.67-1.58 (m, 0.50H), 1.42-1.34 (m5 1.50H), 0.93 (t, J=7.5 Hz, 0.75H), 0.67 (t, J=7.5 Hz, 2.25H). $^{13}$C NMR (101 MHz, DMSO-$d_6$) (mixture of rotamers) δ 165.8, 159.0, 156.6, 154.3, 131.6, 131.0, 128.7, 128.6, 126.3, 119.9, 119.7, 66.6, 66.4, 36.9, 36.4, 36.4, 21.8, 21.5, 10.0, 9.8.

HPLC Analysis: Column: Agilent ZORBAX Eclipse Plus C18 3.5 um 4.6×150 mm; Column Temeprature: 40° C.; Solvent A: 0.01M NH$_4$OOCH in water:MeOH (90:10 v/v); Solvent B: 0.01M NH$_4$OOCH in MeOH:CH$_3$CN (70:30 v/v); Diluent: 0.25 mg/ml in acetonitrile; Gradient: % B:0 min. 10%; 10 min. 30%; 20 min. 90%; 20.1 min. 10%; stop time 25 min; Flow Rate: 1.0 ml/min; Wavelength: 220 nm;

The retention time of 7-fluoro-1-methylindoline-2,3-dione was 10.7 minutes. The retention time of 7-fluoroindoline-2,3-dione was 6.8 minutes. The retention time of 3-fluoro-2-(methylamino)benzoic acid was 5.9 minutes. The retention time of 3-fluoro-2-(methyl(propoxycarbonyl) amino)benzoic acid was 12.0 minutes.

Compound 1

(S)-3-(prop-1-en-2-yl)cyclohexan-1-one

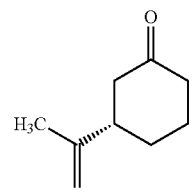

(1)

Catalyst Preparation: Rhodium (I) (S)-(+)-5,5'-bis [di(3,5-di-tert-butyl-4-methoxyphenyl) phosphino]-4,4'-bi-1,3-benzodioxole Methanol (320 mL) was charged into a 0.5 L inerted reactor equipped with an overhead agitator, nitrogen sparging tube and an outlet connected to an oxygen meter. The reactor was inerted by sparging nitrogen subsurface through methanol until <300 ppm O$_2$ was detected in the headspace. S-(+) DTBM-SEGPHOS (77.3 g, 65.6 mmol) and [Rh(cod) Cl]$_2$ (15.4 g, 31 mmol) were charged and the nitrogen sparging continued until <300 ppm O$_2$ was detected in the headspace. The mixture was agitated at room temperature under constant positive nitrogen pressure for 30 min by sweeping a low flow of nitrogen through the headspace. The initial yellow slurry gradually transformed into a deep-red solution containing a small amount of solids (excess ligand). The ligation completion was confirmed by $^{31}$P NMR by disappearance of the ligand peak at 13.1 ppm (s) and the appearance of the new singlets at 26.10 ppm and 27.01 ppm for the ligated species.

Synthesis of the Compound I

A 20 L jacketed Chemglass reactor, equipped with an overhead agitator, a thermocouple, nitrogen sparging tube, a sampling port, a condenser connected to the glycol supply and a nitrogen outlet connected sequentially to a bubbler, flow meter and an oxygen meter, was inerted using a vigorous nitrogen sweep. A Teledyne 3110 oxygen meter was used to monitor the progress of inertion. A vigorous nitrogen sweep was implemented prior to reagent charges until the oxygen reading was <300 ppm.

Heptane (4.0 L), 2-cyclohexen-1-one (1 kg, 10.4 M) in heptane (1.0 L), isopropenyl pinacol boronate (1.92 kg, 11.4 M, 1.1 eq) in heptane (1.0 L), DIPEA (0.91 L, 0.67 kg, 0.50 eq), a solution of 2,2-dimethyl-1,3-propanediol (1.19 kg, 1.1 eq) in methanol (0.12 L) in water (3 L), and additional heptane (2.55 L) were sequentially charged to the reactor via vacuum. Nitrogen sparging subsurface through the agitated biphasic mixture continued after the charges until an oxygen level of <300 ppm was reached in the headspace prior to the catalyst charge. Then the nitrogen flow was reduced to maintain a slight positive pressure in the reactor.

The catalyst light slurry was transferred from the bottom value of the 0.5 L reactor's bottom into the 20 L reactor through an inerted Teflon tubing by applying slight positive pressure of nitrogen. The contents of the small reactor was transferred including the excess of the undissolved solid.

The jacket was set to 60° C. on the 20 L reactor and the biphasic mixture was vigorously heated and agitated under nitrogen at 55-58° C. After the transfer, the nitrogen flow was reduced to maintain a slight positive pressure and to minimize solvent loss. After completion of the reaction, the reaction mixture was cooled to 20-25° C. The phases were separated and the organic phase was washed with 1N HCl aq (v=5.7 L, 0.55 eq) to remove DIPEA, and with water (2.5 L). Two back-extractions with heptane (2×2 L) from the original aqueous phase were performed to bring back an additional 8 mol % of the product. All organic phases were combined and polished filtered back to the cleaned reactor. Heptane was removed under reduced pressure (30-40° C. at 45-55 torr) to give the crude product, which was transferred to a 2 L 4-necked round bottom flask, equipped with a mechanical stirrer, a thermocouple, a 30 cm Vigreaux column, a distillation adapter containing a thermocouple to measure the vapor temperature, a condenser (glycol) and a Teflon tubing attached to a receiver flask. Distillation was performed at a pressure of 10 torr with the main fraction containing the product boiling at 85-92° C. to afford 1.18 kg (85 mol % as is, 82.1% corrected) of (S)-3-(prop-1-en-2-yl)cyclohexan-1-one. Chiral GC: Supelco AlphaDex 120 30×0.25 mm×0.25 μm, inlet 200° C., split ratio 30:1, carrier gas:helium, constant flow 1.9 mL/min, oven program: 80° C. to 110° C. at 2° C./min, then 20° C./min to 220° C., detector: FID 250° C.; RT for the desired product: 14.4 min. Chemical purity: 97.1 GCAP. Chiral purity: ee=99.6%. $^1$H NMR (CDCl$_3$): 1.57-1.70 (m, 12H), 1.75 (s, 3H), 1.91-1.96 (m, 1H), 2.05-2.12 (m, 1H), 2.26-2.46 (m, 5H), 4.73 (s, 1H), 4.78 (s, 1H).

Compound 2

(S,E)-4-bromo-5-fluoro-2-(2-(3-(prop-1-en-2-yl)cyclohexylidene)hydrazinyl)benzoic acid

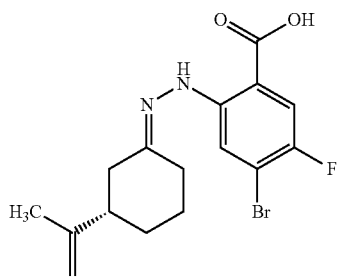

(2)

(S)-3-(prop-1-en-2-yl)cyclohexan-1-one (50.00 mL, 33.4 mmol, 0.667 mmol/mL) solution in heptane was added to a Chemglass reactor. Next, 75 mL of MeOH was added. The MeOH solution was distilled at 60 torr/50° C. jacket temperature and 75 mL of constant volume with the addition of 300 mL of MeOH. The contents of the reactor were cooled to 20° C. 2-amino-4-bromo-5-fluorobenzoic acid (8.5415 g, 29.918 mmol) was added to the reactor. The reaction mixture was stirred at 20° C. After, 30 minutes, the solid material was dissolved to form a clear brown solution. After 2.0 h, water (25.0 mL) was added over 25 min to the reaction mixture under slow agitation (RPM=100). After an additional 1.0 h, the slurry was filtered (fast; <3 seconds). The cake was washed with 2×25 mL of MeOH/H$_2$O (3:2). The cake was dried at 55° C. under vacuum overnight to afford (S,E)-4-bromo-5-fluoro-2-(2-(3-(prop-1-en-2-yl)cyclohexylidene) hydrazinyl)benzoic acid (10.5701 g; 95.7% yield). HPLC method: Column: Zorbax Eclipse plus 1.8 um C8 (4.6×50 mm); injection volume: 10 μL; Mobile Phase A: 0.05% TFA in acetonitrile:water (5:95, v/v); Mobile Phase B: 0.05% TFA in water:acetonitrile (5:95, v/v); Gradient (% B) 0 min (30%), 14 min (100%), 15 min (30%); Flow Rate: 1.0 mL/min; Wavelength: 240 nm for IPC; Column temp: 25° C.; IPC Sample Prep: Dissolved 10 μL of the reaction mixture and dilute with MeOH to 1.5 mL; HPLC results: Intermediate A2, 0.87 min; Compound 2, 9.97 min. $^1$HNMR (400 MHz, DMSO-d$_6$) δ13.54 (s, 1H), 10.76 (d, J=26.5 Hz, 1H), 7.73 (appt triplet, J=6.32 Hz, 1H), 7.64 (dd, J=9.35, 1.26 Hz, 1H), 4.77-4.75 (m, 2H), 2.68-2.61 (m, 1H), 2.46-2.44 (m, 1H), 2.27-2.12 (m, 2H), 2.06-1.97 (m, 1H), 1.96-1.86 (m, 1H), 1.82-1.80 (m, 1H), 1.75-1.74 (m, 3H), 1.50-1.41 (m, 2H). $^{13}$C NMR (100 MHz, DMSO-d$_6$) δ168.67, 152.76, 152.73, 150.71, 148.41, 148.38, 148.20, 145.10, 117.45, 117.21, 116.45, 116.40, 115.76, 115.74, 115.54, 115.52, 109.64, 109.39, 108.88, 108.85, 108.83, 108.80, 44.80, 43.72, 34.22, 30.89, 30.08, 30.05, 25.42, 25.39, 24.15, 20.60, 20.44.

Compound 3

(S)-5-bromo-6-fluoro-2-(prop-1-en-2-yl)-2,3,4,9-tetrahydro-1H-carbazole-8-carboxylic acid

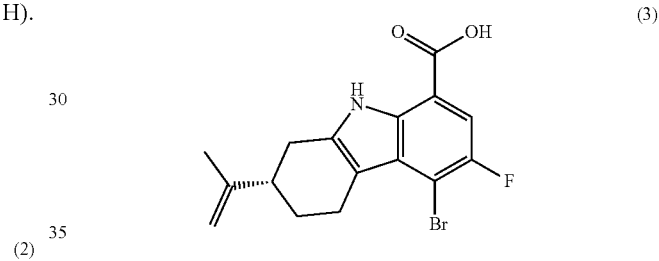

(3)

Zinc chloride (8.7858 g, 64.46 mmol) and (S,E)-4-bromo-5-fluoro-2-(2-(3-(prop-1-en-2-yl)cyclohexylidene)hydrazinyl)benzoic acid (17.0011 g, 46.05 mmol) were added to a Chemglass reactor. Next, isopropyl acetate (170 mL) was added. The contents of the reactor were heated at 69.5° C. for 71 h and then cooled to room temperature. 2-MeTHF (205 mL) and HCl (1 mol/L) in water (85 mL) were added. The reaction mixture was stirred at room temperature for 0.5 h. The layers were allowed to separate. The organic layer was washed with water (85 mL). The layers were separated and the organic layer was polish-filtered. The rich organic layer was distilled at 220 torr and 70° C. jacket temperature to 85 mL (5.0 mL/g (S,E)-4-bromo-5-fluoro-2-(2-(3-(prop-1-en-2-yl)cyclohexylidene)hydrazinyl) benzoic acid). Next, the solution was distilled at 120 mL (7.0 mL/g (S,E)-4-bromo-5-fluoro-2-(2-(3-(prop-1-en-2-yl)cyclohexylidene) hydrazinyl) benzoic acid) constant volume under 220 torr and 70° C. jacket temperature with continuous addition of acetonitrile (350 mL, 20 mL/g). Additional CH$_3$CN was added to make the slurry volume=153 mL (9.0 mL/g (S,E)-4-bromo-5-fluoro-2-(2-(3-(prop-1-en-2-yl)cyclohexylidene) hydrazinyl)benzoic acid). The slurry was heated to 82° C. batch temperature. After 3.0 h, the slurry was cooled to 20° C. over 2.0 h. The slurry was stirred at 20° C. for an additional 14 h. The slurry was filtered and the cake was washed with acetonitrile (2×17 mL, 1.0 mL/g (S,E)-4-bromo-5-fluoro-2-(2-(3-(prop-1-en-2-yl)cyclohexylidene) hydrazinyl)benzoic acid). The wet cake was dried in a vacuum oven at a temperature range of 50-55° C. overnight to afford (S)-5-bromo-6-fluoro-2-(prop-1-en-2-yl)-2,3,4,9-tetrahydro-1H-carbazole-8-carboxylic acid (7.8991 g;

48.7% yield). HPLC method: Column: Agilent Zorbax Eclipse plus 1.8 μm C8 (4.6×50 mm); Injection Volume: 10 μL; Mobile Phase A: 0.05% TFA in acetonitrile:water (5:95, v/v); Mobile Phase B: 0.05% TFA in water:acetonitrile (5:95, v/v); Gradient (% B) 0 min (30%), 14 min (100%), 15 min (100%); Flow Rate: 1.0 mL/min; Wavelength: 240 nm for IPC and Isolated product; Column temp: 25° C.; IPC Sample Prep: 1 mL/100 mL in tetrahydrofuran; Isolated Sample Prep: 0.25 mg/mL in tetrahydrofuran; HPLC results: Compound 3, 8.86 min; Compound 2, 10.0 min. $^1$H NMR (400 MHz, DMSO-$d_6$) δ13.41 (s, 1H), 11.03 (s, 1H), 7.45 (d, J=9.85 Hz, 1H), 4.79 (appt d, J=4.55Hz, 2H), 3.21-3.17 (m, 1H), 2.95 (dd, J=17.18, 4.80 Hz, 1H), 2.91-2.83 (m, 1H), 2.61 (dd, J=16.93, 10.61 Hz, 1H), 2.41-2.35 (m, 1H), 2.01-1.95 (m, 1H), 1.79 (s, 3H), 1.67-1.57 (m, 1H). $^{13}$C NMR (100 MHz, DMSO-$d_6$) δ 166.64, 166.61, 152.72, 150.42, 148.44, 139.96, 131.90, 127.44, 127.43, 112.40, 112.33, 109.67, 109.54, 109.39, 109.19, 109.14, 28.28, 27.79, 22.20, 20.69.

Compound 4

(S)-5-bromo-6-fluoro-2-(prop-1-en-2-yl)-2,3,4,9-tetrahydro-1H-carbazole-8-carboxamide

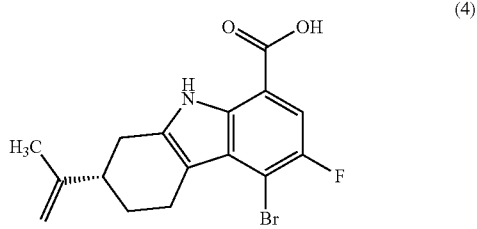 [SMILES: C=C(C)[C@H]1CCc2c([nH]c3c(C(=O)O)cc(F)c(Br)c23)C1]

Acetonitrile (70 mL) was added to a Chemglass reactor, followed by the addition of (S)-5-bromo-6-fluoro-2-(prop-1-en-2-yl)-2,3,4,9-tetrahydro-1H-carbazole-8-carboxylic acid (7.0150 g). Next, 1,1'-carbonyldiimidazole (4.2165 g, 26.004 mmol) was added. The reaction mixture was stirred (RPM=100) for 5.0 hr at 20° C. The slurry was cooled to 3° C. Ammonia (30 mL, 200 mmol, 30 mass %) was added in less than 2 min. The slurry was stirred at 3° C. for 17.5 h. Water (70 mL) was added over 5 min. The slurry was stirred at 3° C. for 3 h. The slurry was filtered and the wet cake was washed with 2×50 mL of CH$_3$CN/H$_2$O (1:1). The wet cake was dried at 55° C. under vacuum overnight to afford (S)-5-bromo-6-fluoro-2-(prop-1-en-2-yl)-2,3,4,9-tetrahydro-1H-carbazole-8-carboxamide (5.2941 g; 75.8% yield). HPLC Method; Column: Agilent Zorbax Eclipse plus 1.8 μm C8 (4.6×50 mm); Injection Volume: 10 μL; Mobile Phase A: 0.05% TFA in acetonitrile:water (5:95, v/v); Mobile Phase B: 0.05% TFA in water:acetonitrile (5:95, v/v); Gradient (% B) 0 min (0%), 8 min (100%), 10 min (100%); Flow Rate: 1.0 mL/min; Wavelength: 240 nm for IPC and Isolated product; Column temp: 25° C.; IPC Sample Prep: Dissolved 10 μL of the reaction mixture into 1.0 mL 0.05 v % DBU/MeOH; Product sample preparation: Dissolved product in MeOH at 1 mg/mL; HPLC results: Compound 4, 6.39 min; Compound 3, 6.80 min. $^1$H NMR (400 MHz, DMSO-$d_6$) δ 11.05 (s, 1H), 8.11 (s, 1H), 7.59 (d, J=10.36 Hz, 1H), 7.55 (br s, 1H), 4.78 (br s, 2H), 3.18 (br d, J=14.65 Hz, 1H), 2.94 (dd, J=16.93, 4.80 Hz, 1H), 2.88-2.82 (m, 1H), 2.62 (dd, J=16.93, 10.61 Hz, 1H), 2.40-2.34 (m, 1H), 1.98 (d, J=11.87 Hz, 1H), 1.78 (s, 3H), 1.66-1.56 (m, 1H). $^{13}$C NMR (100 MHz, DMSO-$d_6$) δ167.64, 152.68, 150.38, 148.47, 139.47, 131.71, 127.02, 127.01, 115.36, 115.28, 109.53, 108.66, 108.61, 107.47, 107.19, 28.24, 27.87, 22.21, 20.67.

Compound 5

(S)-5-bromo-6-fluoro-2-(2-hydroxypropan-2-yl)-2,3,4,9-tetrahydro-1H-carbazole-8-carboxamide

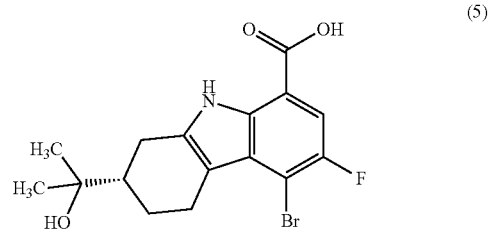 [SMILES: CC(C)(O)[C@H]1CCc2c([nH]c3c(C(=O)O)cc(F)c(Br)c23)C1]

Dichloromethane (100 mL) and (S)-5-bromo-6-fluoro-2-(prop-1-en-2-yl)-2,3,4,9-tetrahydro-1H-carbazole-8-carboxamide (PPP, 10.0016 g, 28.48 mmol) were added to a 250 mL Chemglass reactor. The slurry was cooled to 5° C. Next, trifluoroacetic acid (14.68 g, 128.7 mmol) was added over 0.5 h with agitation (RPM=250) while maintaining the internal temperature at less than 10° C.). The temperature was raised to 14° C. and the reaction mixture was stirred at 14° C. for 17.5 h. Next, 60 mL of MeOH was added to dissolve the thin slurry. The solution was cooled to −10° C. The solution was distilled at 80 torr while the jacket temperature was gradually raised from −10° C. to 20° C. The solution was distilled to about 60 mL volume. The internal temperature changed from −7° C. to −2° C. The solution became a heavy slurry. The distillation was continued at 80 torr at 20° C. jacket temperature at 60 mL volume with the addition of 120 mL MeOH. The internal temperature changed from −2° C. to 15° C. The solution became a heavy slurry. The distillation became slow. The vacuum pressure was changed to 60 torr, and the distillation was continued with a 20° C. jacket temperature to 40 mL slurry volume. The batch temperature went from 12° C. to 13° C.

MeOH (20 mL) was sprayed to wash solid crust off the reactor wall, but was not effective. Aqueous NH$_3$ (30.0 mL, 400 mmol, 28 mass %) was sprayed to the slurry (pH=10.59). Some solid crust on the upper reactor wall still remained. The slurry was stirred at 20° C. for 0.5 h (pH=10.58), then heated to 70° C. in 15 min. All the solid crust on the upper reactor wall dissolved. Next, water (40 mL) was added over a period of 15 min. The solution remained as a clear solution at 70° C.

The slurry was seeded with solid (S)-5-bromo-6-fluoro-2-(2-hydroxypropan-2-yl)-2,3,4,9-tetrahydro-1H-carbazole-8-carboxamide (~5 mg). The seeds remained but there was little additional crystallization was observed at 70° C. The slurry was heated at 70° C. (jacket temperature=80° C.) for 0.5 h, and then cooled down to 20° C. in 0.5 h. At 65° C. the mixture became cloudy. The mixture was stirred at 20° C. for 65 h. The mixture was filtered. The cake was washed with 2×15 mL of MeOH/H$_2$O (1:1). The wet cake was dried at 65° C. under vacuum for 24 h, giving (S)-5-bromo-6-fluoro-2-(2-hydroxypropan-2-yl)-2,3,4,9-tetrahydro-1H-carbazole-8-carboxamide (9.1741 g, 87.3% yield).

(S)-5-bromo-6-fluoro-2-(2-hydroxypropan-2-yl)-2,3,4,9-tetrahydro-1H-carbazole-8-carboxamide was recrystallization in MeOH/MTBE/n-Heptane (1:4:8).

(S)-5-bromo-6-fluoro-2-(2-hydroxypropan-2-yl)-2,3,4,9-tetrahydro-1H-carbazole-8-carboxamide (8.0123 g) was added to a reactor. Next, MeOH (8.0 mL) and MTBE (32.0 mL) were added. The mixture was heated to 45° C. to dissolve the slurry. Heptane (64 mL) was added over a period of 15 min at 45° C. The slurry was stirred at 45° C. for an additional 0.5 h and then cooled to 5° C. in 1.0 h. Stirring was continued at 5° C. for an additional 1.0 h. The slurry was filtered and the wet cake was washed with 2×20 mL of n-heptane. The wet cake was dried at 65° C. under vacuum for 16 h to afford (S)-5-bromo-6-fluoro-2-(2-hydroxypropan-2-yl)-2,3,4,9-tetrahydro-1H-carbazole-8-carboxamide (6.9541 g; 86.8%).

(S)-5-bromo-6-fluoro-2-(2-hydroxypropan-2-yl)-2,3,4,9-tetrahydro-1H-carbazole-8-carboxamide (8.0123 g) was added to a reactor. Next, MeOH (8.0 mL) and MTBE (32.0 mL) were added. The mixture was heated to 45° C. to dissolve the slurry. Heptane (64 mL) was added over a period of 15 min at 45° C. The slurry was stirred at 45° C. for an additional 0.5 h and then cooled to 5° C. in 1.0 h. Stirring was continued at 5° C. for an additional 1.0 h. The slurry was filtered and the wet cake was washed with 2×20 mL of n-heptane. The wet cake was dried at 65° C. under vacuum for 16 h to afford (S)-5-bromo-6-fluoro-2-(2-hydroxypropan-2-yl)-2,3,4,9-tetrahydro-1H-carbazole-8-carboxamide (6.9541 g; 86.8%). HPLC method Column: Phenomenex Kinetex C18 2.6 um 100A 4.6×150 mm SN: 538219-97; Injection Volume 5 µL; Mobile Phase A: 0.05% TFA in acetonitrile:water (5:95, v/v); Mobile Phase B: 0.05% TFA in water:acetonitrile (5:95, v/v); Gradient (% B) 0 min (32%), 5 min (38%), 11 min (38%), 18 min (68%), 22 min (68%), 30 min (90%), 31 min (100%); Flow Rate: 1.0 mL/min; Wavelength: 220 nm for IPC and Isolated product; Column temp: 25° C.; IPC Sample Prep: 1 µL/1 mL in tetrahydrofuran; Isolated Sample Prep: 0.25 mg/mL in tetrahydrofuran; HPLC results: Compound 5, 9.58 min; Compound 4, 19.98 min; $^{1}$H NMR (400 MHz, DMSO-$d_6$) δ 10.99 (s, 1H), 8.10 (s, 1H), 7.57 (d, J=10.36 Hz, 1H), 7.54 (br s, 1H), 4.27 (s, 1H), 3.26 (dd, J=15.66, 4.29 Hz, 1H), 2.93 (dd, J=17.18, 4.55 Hz, 1H), 2.76-2.68 (m, 1H), 2.44 (dd, J=16.17, 11.87 Hz, 1H), 2.12 (br d, J=11.12 Hz, 1H), 1.69-1.62 (m, 1H), 1.31 (ddd, J=25.01, 12.38, 5.31 Hz, 1H), 1.14 (s, 6H). $^{13}$C NMR (100 MHz, DMSO-$d_6$) δ 167.67, 152.64, 150.34, 140.46, 131.77, 127.03, 127.02, 115.28, 115.21, 109.09, 109.05, 107.30, 107.03, 101.43, 101.19, 70.37, 44.96, 27.17, 26.73, 24.88, 24.36, 22.85.

Compound 6

(2S)-5-(3-amino-2-methylphenyl)-6-fluoro-2-(2-hydroxypropan-2-yl)-2,3,4,9-tetrahydro-1H-carbazole-8-carboxamide

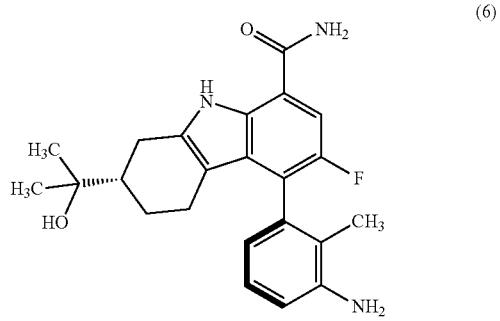

(6)

Catalyst Activation

Into a 1 Liter Chemglass reactor (Reactor A) were added Me-THF (4 L/kg) followed by (R)-BINAP (0.0550 mol/mol, 7.45 mmol) and Pd(OAc)$_2$ (0.0500 mol/mol, 6.77 mmol). Additional Me-THF (1 L/kg) was added. The mixture was stirred at 25° C. for 1 h. Next, 4-bromo-3-fluoro-7-(1-hydroxy-1-methyl-ethyl)-6,7,8,9-tetrahydro-5H-carbazole-1-carboxamide (0.10 equiv, 13 mmol) was added into the mixture in Reactor A, followed by the addition of 2-methyltetrahydrofuran (0.50 L/kg) and water (0.5 L/kg). The overhead space of Reactor A was sparged with nitrogen at 1 mL/second for 40 min at 25° C. The resulting mixture was then stirred at 70° C. for 3 h under a positive pressure of nitrogen (1.05 atm). The resulting mixture containing the activated catalyst was cooled to 25° C. and kept at 25° C. under a positive pressure of nitrogen before use.

To a 500 mL Chemglass reactor (Reactor B) were added water (6 L/kg) followed by K$_3$PO$_4$ (6 equiv., 813 mmol). The addition was exothermic. The mixture was stirred till the base was fully dissolved. The overhead space of Reactor B was sparged with nitrogen at 1 mL/second for 60 min at 25° C. The K$_3$PO$_4$ solution in Reactor B was then kept under a positive pressure of nitrogen before use.

To Reactor A, which contained the activated catalyst, was added 4-bromo-3-fluoro-7-(1-hydroxy-1-methyl-ethyl)-6,7,8,9-tetrahydro-5H-carbazole-1-carboxamide (0.90 equiv., 122 mmol), followed by THF (2.5 L/kg). Then (3-amino-2-methyl-phenyl)boronic acid hydrochloride (1.15 equiv., 156 mmol) and MeOH (2 L/kg) were added to Reactor A. The overhead space of Reactor A was sparged with nitrogen at 1 mL/second for 40 min. Then the reaction mixture in Reactor A was cooled to −10° C. under a positive pressure of nitrogen.

The K$_3$PO$_4$ aqueous solution in Reactor B was then transferred into Reactor A via a cannula while both reactors were kept under a positive pressure of N$_2$. The rate of transfer was controlled so that the inner temperature in Reactor A was below 0° C. throughout the operation.

The resulting biphasic reaction mixture was stirred at 5° C. under a positive pressure of nitrogen. After 2.5 h at 5° C., HPLC analysis of the reaction mixture showed 0.3 AP starting material remained. The reaction mixture was then warmed to 25° C. and stirred at 25° C. for 30 min. HPLC analysis of the reaction mixture showed 0.0 AP starting material remained.

N-acetyl-L-cysteine (1 kg/kg, 306 mmol) and water (2.5 L/kg) were added into Reactor A. The resulting mixture was stirred at 40° C. for 2 h then cooled to 25° C. The bottom layer (aqueous layer) was discharged and the top layer (organic layer) was retained in the reactor.

Afterwards, THF (1 L/kg) and NaCl solution (13 mass %) in water (7 L/kg) were added into Reactor A, and the resulting mixture was stirred at 25° C. for 1 h. The bottom layer (aqueous layer) was discharged and the top layer (organic layer) was retained in the reactor.

The organic layer was filtered through a polyethylene filter. Then the reactor was rinsed with Me-THF (0.50 L/kg). The rinse was filtered through the polyethylene filter and combined with the filtrate. The solution was transferred into a clean 1 L reactor (Reactor C).

The mixture in Reactor C was concentrated under reduced pressure to 8.8 L/kg. (2 L/kg solvent was removed by distillation). At 50° C., n-BuOH (4 L/kg) was added slowly over 2 h. The mixture was then stirred at 50° C. for 2.5 h, and a slurry was obtained.

The solvent was swapped to n-BuOH through constant volume distillation. During this operation, n-BuOH (8 L/kg) was used and 8 L/kg solvent was removed from Reactor C. The resulting mixture was stirred at 55° C. for 1 h and cooled to 25° C. over 1 h.

The slurry in Reactor C was filtered. The reactor rinsed with n-BuOH (2 L/kg). The cake was then washed with this reactor rinse, followed by heptane (8 L/kg). The product was dried under vacuum at 55° C. for 24 h to afford (2S,5R)-5-(3-amino-2-methylphenyl)-6-fluoro-2-(2-hydroxypropan-2-yl)-2,3,4,9-tetrahydro-1H-carbazole-8-carboxamide, which was isolated as an off-white solid powder (46.2 g, 86% yield). HPLC analysis: (2S,5R)-5-(3-amino-2-methylphenyl)-6-fluoro-2-(2-hydroxypropan-2-yl)-2,3,4,9-tetrahydro-1H-carbazole-8-carboxamide:98.1 AP (19.2 min); (2S,5S)-5-(3-amino-2-methylphenyl)-6-fluoro-2-(2-hydroxypropan-2-yl)-2,3,4,9-tetrahydro-1H-carbazole-8-carboxamide:1.8 AP (19.9 min), (S)-6-fluoro-2-(2-hydroxypropan-2-yl)-2,3,4,9-tetrahydro-1H-carbazole-8-carboxamide:0.1 AP (20.9 min). Column: Waters XBridge BEH C18 S-2.5 um 150×4.6 mm; Solvent A: 10 mM sodium phosphate buffer pH 7; Solvent B: $CH_3CN$:MeOH (50:50 v/v); Gradient: % B: 0 Min. 5%; 4 Min. 30%; 41 Min. 95%; 47 Min. 95%; Stop Time: 48 min; Flow Rate: 0.7 ml/min wavelength: 240 nm. $^1$H NMR (500 MHz, DMSO-$d_6$) δ 10.76 (s, 1H), 8.09 (br s, 1H), 7.54 (d, J=10.7 Hz, 1H), 7.47 (br s, 1H), 6.96 (t, J=7.7 Hz, 1H), 6.72 (d, J=7.9 Hz, 1H), 6.41 (d, J=7.3 Hz, 1H), 4.90 (s, 2H), 4.19 (s, 1H), 2.91 (br dd, J=16.6, 4.0 Hz, 1H), 2.50-2.39 (m, 1H), 2.05-1.93 (m, 1H), 1.88-1.75 (m, 5H), 1.64-1.53 (m, 1H), 1.21-1.11 (m, 1H), 1.09 (s, 6H). $^{13}$C NMR (126 MHz, DMSO-$d_6$) δ 169.0 (d, J=2.7 Hz), 152.5 (d, J=229.8 Hz), 146.7, 139.1, 134.4, 132.0, 127.7 (d, J=4.5 Hz), 125.6, 123.3 (d, J=20.0 Hz), 120.5, 119.2, 115.1 (d, J=7.3 Hz), 114.3, 109.5 (d, J=4.5 Hz), 107.2 (d, J=27.3 Hz), 70.9, 45.9, 27.6, 27.2, 25.3, 25.0, 22.7, 14.7.

Compound 7 propyl (2-((3-((2S)-8-carbamoyl-6-fluoro-2-(2-hydroxypropan-2-yl)-2,3,4,9-tetrahydro-1H-carbazol-5-yl)-2-methylphenyl)carbamoyl)-6-fluorophenyl)(methyl)carbamate (7)

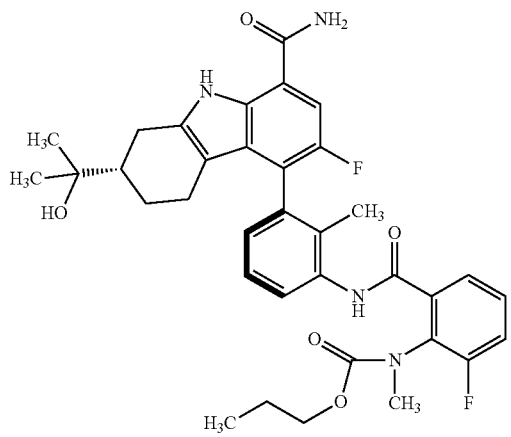

N,N-Dimethylformamide (7.0 L, 7 L/kg) was charged into a reactor followed by the addition of (2S)-5-(3-amino-2-methylphenyl)-6-fluoro-2-(2-hydroxypropan-2-yl)-2,3,4,9-tetrahydro-1H-carbazole-8-carboxamide (1 kg, 2528 mmol, 1.0 eq.). 3-Fluoro-2-(methyl(propoxycarbonyl)amino)benzoic acid (0.774 kg, 3034 mmol, 1.2 eq.) was added to the reactor, followed by the addition of 1-methylimidazole (0.267 kg, 3287 mmol, 1.3 eq) and methanesulfonic acid (0.122 kg, 1264 mmol, 0.5 eq.) at 20° C. The reaction mixture was stirred for at 20° C. for 30 min to completely dissolve the reaction contents. The reaction mixture was cooled to 10° C. and EDAC (1-(3-dimethylaminopropyl)-3-ethylcarbodiimide hydrochloride) (0.679 kg, 3540 mmol, 1.4 eq) was charged into the reactor. An exotherm of approximately 4° C. was observed. The reaction mixture was stirred at 10° C. for 4 h.

After 4 hrs, the reaction mixture was warmed to 20° C. Isopropyl acetate (25 L, 25 L/kg) was added to the reaction mixture followed by 25 wt % aqueous sodium chloride solution (2.5 L, 2.5 L/kg) and 1.0 M aqueous hydrochloric acid (2.5 L, 2.5 L/kg). The reaction mixture was stirred for 30 min. The agitation was stopped and the bottom aqueous layer was separated. Water (5 L, 5 L/kg) was charged to the rich organic solution and stirred for 30 min. The agitation was stopped and the bottom aqueous layer was separated. Next, 2.5% aqueous sodium bicarbonate solution (10 L, 10 L/kg) was charged to the rich organic solution and stirred for 30 min. The agitation was stopped and the bottom aqueous layer was separated. Water (10 L, 10 L/kg) was charged to the rich organic solution and stirred for 30 min. The agitation was stopped and the bottom aqueous layer was separated. The rich organic solution was concentrated under reduced pressure (90 mbar and 40° C. jacket temperature) to 7 L/kg volume. Dichloromethane (5 L, 5 L/kg) was charged to the product rich isopropyl acetate solution at 20° C. Seeds of propyl (2-((3-((2S)-8-carbamoyl-6-fluoro-2-(2-hydroxypropan-2-yl)-2,3,4,9-tetrahydro-1H-carbazol-5-yl)-2-methylphenyl)carbamoyl)-6-fluorophenyl)(methyl)carbamate (10 g, 1%) were charged and a thin slurry formed. Heptane (7 L, 7 L/kg) was charged to the above slurry slowly over 1 hr at 25° C. and stirred for another 1 h before cooling 20° C. over 30 min. The resultant slurry was stirred for 4-6 hrs at 20° C. The slurry was filtered over a laboratory Buchner funnel. The wet cake was washed with a dichloromethane-heptane mixture (10:7 ratio, 12 vol). The wet cake was dried in a vacuum oven at 25 mm Hg vacuum and 50° C. until the residual heptane was <13 wt % in the solid to provide 1.5 kg of propyl (2-((3-((2S)-8-carbamoyl-6-fluoro-2-(2-hydroxypropan-2-yl)-2,3,4,9-tetrahydro-1H-carbazol-5-yl)-2-methylphenyl)carbamoyl)-6-fluorophenyl)(methyl) carbamate in 94% yield. The product was a mixture of four amide rotational isomers. $^1$H NMR (400 MHz, DMSO-$d_6$) δ 10.79 (br s, 1H), 9.96 (m, 1H), 8.07 (br s, 1H), 7.50 (m, 6H), 7.29 (m, 1H), 7.09 (m, 1H), 4.15 (m, 1H), 3.89 (m, 2H), 3.19 (br s, 1H), 3.13 (br s, 2H), 2.90 (m, 1H), 2.44 (m, 1H), 1.97 (m, 3H), 1.82 (m, 3H), 1.50 (m, 3H), 1.26 (m, 5H), 1.09 (m, 7H), 0.85 (m, 4H), 0.70 (m, 2H). $^{13}$C NMR (101 MHz, DMSO-$d_6$) δ 168.33, 168.32, 164.85, 164.55, 159.38, 159.16, 156.93, 156.69, 154.90, 154.74, 153.14, 150.86, 139, 15, 139.11, 137.96, 137.89, 137.36, 137.23, 135.75, 135.68, 135.64, 134.77, 134.68, 132.57, 132.51, 132.46, 132.42, 131.50, 128.98 (m), 128.26 (m), 127.05, 127.01, 125.99, 125,76, 124.97, 124.83, 124.06, 121.48, 121.40, 121.28, 121.20, 117.90, 117.86, 117.70, 117.65, 115.19, 115.15, 115.12, 115.07, 108.69, 108.65, 106.87, 106.60, 70.39, 66.83, 66.80, 66.73, 45.32, 37.38, 37.15, 31.23, 28.35, 27.05, 26.68, 24.85, 24.61, 22.27, 22.07, 21.84, 21.75, 14.98, 14.93, 14.86, 14.84, 13.87, 10.11, 9.89.

HPLC Analysis: Column: Zorbax Eclipse Plus C18 3.5 um, 150×4.6 mm ID; Solvent A: 10 mM ammonium formate in water-MeOH (90:10); Solvent B: $CH_3CN$:MeOH (30:70 v/v); Gradient: % B: 0 Min. 50%; 25 Min. 81%; 26 Min. 100%; 30 Min. 100%; Stop Time: 30 min; Flow Rate: 1 ml/min; Wavelength: 240 nm. The retention time of propyl (2-((3-((2S)-8-carbamoyl-6-fluoro-2-(2-hydroxypropan-2- yl)-2,3,4,9-tetrahydro-1H-carbazol-5-yl)-2-methylphenyl) carbamoyl)-6-fluorophenyl)(methyl) carbamate was 14.6 min. The retention time of 3-fluoro-2-(methyl(propoxycarbonyl) amino)benzoic acid was 2.6 min. The retention time of (2S)-5-(3-amino-2-methylphenyl)-6-fluoro-2-(2-hydroxypropan-2-yl)-2,3,4,9-tetrahydro-1H-carbazole-8-carboxamide was 6.1 min.

Compound 8

6-fluoro-5-(R)-(3-(S)-(8-fluoro-1-methyl-2,4-dioxo-1,2-dihydroquinazolin-3(4H)-yl)-2-methylphenyl)-2-(S)-(2-hydroxypropan-2-yl)-2,3,4,9-tetrahydro-1H-carbazole-8-carboxamide

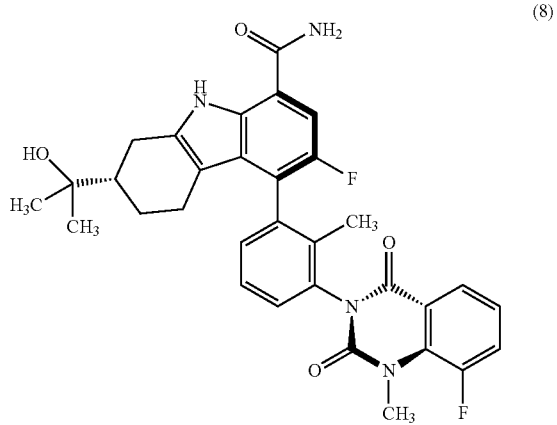

(8)

To a 1 L round bottom flask with stir bar was added propyl (2-((3-((2S)-8-carbamoyl-6-fluoro-2-(2-hydroxypropan-2-yl)-2,3,4,9-tetrahydro-1H-carbazol-5-yl)-2-methylphenyl) carbamoyl)-6-fluorophenyl)(methyl)carbamate (100 g, 148 mmol, 93.5 mass %) followed by MeTHF (500 mL, 4990 mmol, 100 mass %). The mixture was stirred at room temperature for 10 minutes to ensure complete dissolution. Next, 150 mL of MeTHF was added, and an azeotropic distillation to remove water was performed at 50° C. and 70 torr. The KF was measured to be 424 ppm. This solution is termed the "Compound 8 solution."

To a 2 L Chemglass reactor was charged MeTHF (2000 mL, 19900 mmol, 100 mass %) followed by lithium tert-butoxide (7.9 mL, 7.9 mmol, 1 mol/L). The KF of MeTHF was measured to be 622 ppm. The Compound 8 solution was added dropwise over 2 hours at room temperature via a Simdos pump. After the addition was complete, the reaction mixture was maintained at temperature for 15 minute.

MeOH (200 mL, 4940 mmol, 100 mass %) was then added to the reactor followed by the addition of acetic acid (0.5 mL, 9 mmol, 100 mass %). The reaction mixture was distilled to 5 volumes of organics (60 mbar pressure, jacket temperature=40° C.). After the distillation, acetone (150 mL, 2000 mmol, 100 mass %) was added to the thick slurry as the solution warmed to 35° C. Once at 35° C., MeOH (550 mL, 13600 mmol, 100 mass %) was charged to the reactor, re-dissolving the batch to provide a yellow solution. The reaction mixture was cooled over 1 hour to 20° C. resulting in crystallization of the product. Ten heat cycles were performed. Starting at 20° C., the batch was heated to 35° C. over 45 minutes, held at 35° C. for 10 minutes, cooled 20° C. over 60 minutes, and held at 20° C. for 10 minutes. After the heat cycles, the slurry was maintained at room temperature for 1 hour at room temperature. Heptane (1100 mL, 7510 mmol, 100 mass %) was added over 4 hours at 20° C. with agitation via a Simdos pump. After the addition, the slurry aged to 20° C. overnight. The product was isolated by vacuum filtration and washed twice with MeOH (200 mL, 4940 mmol, 100 mass %). The product was dried on a filter with vacuum for 1.5 h to afford 6-fluoro-5-(R)-(3-(S)-(8-fluoro-1-methyl-2,4-dioxo-1,2-dihydroquinazolin-3(4H)-yl)-2-methylphenyl)-2-(S)-(2-hydroxypropan-2-yl)-2,3,4,9-tetrahydro-1H-carbazole-8-carboxamide at 89.4% corrected yield (80.52 g, 6 wt % MeOH, Purity by HPLC: 99.32 AP; Retention time (11.65 min)).

$^1$H NMR (500 MHz, DMSO-d$_6$) 10.78 (s, 1H), 8.07 (br. s., 1H), 7.95 (d, J=7.8 Hz, 1H), 7.72 (dd, J=14.2, 8.0 Hz, 1H), 7.56 (d, J=10.8 Hz, 1H), 7.45 (br. s., 1H), 7.42-7.36 (m, 1H), 7.34 (d, J=6.9 Hz, 1H), 7.34-7.31 (m, 1H), 7.29 (dd, J=7.5, 1.3 Hz, 1H), 4.17 (s, 1H), 3.73 (d, J=8.0 Hz, 3H), 2.91 (dd, J=16.8, 4.4 Hz, 1H), 2.48-2.37 (m, 1H), 1.98-1.89 (m, 2H), 1.87 (d, J=11.0 Hz, 1H), 1.76 (s, 3H), 1.59 (td, J=11.5, 4.1 Hz, 1H), 1.20-1.12 (m, 1H), 1.11 (s, 6H).

$^{13}$C NMR (126 MHz, DMSO-d$_6$) 168.2 (d, J=1.8 Hz, 1C), 160.1 (d, J=3.6 Hz, 1C), 151.9 (d, J=228.9 Hz, 1C), 150.5 (d, J=41.8 Hz, 1C), 148.7 (d, J=205.3 Hz, 1C), 139.2, 135.1, 135.0, 134.8, 131.4, 130.6, 130.0 (d, J=7.3 Hz, 1C), 128.5, 127.1 (d, J=4.5 Hz, 1C), 125.7, 124.3 (d, J=2.7 Hz, 1C), 123.6 (d, J=8.2 Hz, 1C), 123.0 (d, J=23.6 Hz, 1C), 120.8 (d, J=20.0 Hz, 1C), 118.4, 115.3 (d, J=7.3 Hz, 1C), 108.8 (d, J=5.4 Hz, 1C), 106.7 (d, J=28.2 Hz, 1C), 70.4, 45.4, 34.3 (d, J=14.5 Hz, 1C), 27.1, 26.8, 24.8, 24.7, 22.1, 14.5.

HPLC Analysis: Column: Chiralcel OX-3R 3 um 4.6×150 mm; Oven Temperature: 50° C.; Solvent A: 0.05% TFA Water/ACN (95:5); Solvent B: 0.05% TFA Water/ACN (5:95); Gradient % B: 0 Min. 0%; 7 Min. 55%; 11 Min. 55%; 14 Min. 100%; Stop Time: 17 Min.; Flow Rate: 1.5 ml/min; wavelength: 225 nm. (2-((3-((2S)-8-carbamoyl-6-fluoro-2-(2-hydroxypropan-2-yl)-2,3,4,9-tetrahydro-1H-carbazol-5-yl)-2-methylphenyl)carbamoyl)-6-fluorophenyl)(methyl) carbamate:0.00 AP (9.85 min).

Alternative Preparation of Compound 8

To a 2.5 L Chemglass reactor with agitator were added 2-Me-THF (162.4 g, 1885 mmol, 100 mass %, 189 mL, 11.83) and DMF (179.5 g, 2456 mmol, 100 mass %, 190 mL, 15.41), followed by the addition of (2S)-5-(3-amino-2-methylphenyl)-6-fluoro-2-(2-hydroxypropan-2-yl)-2,3,4,9-tetrahydro-1H-carbazole-8-carboxamide (63.03 g, 63.03 mL, 159.4 mmol, 63.03 g), 3-fluoro-2-(methyl(propoxycarbonyl)amino)benzoic acid (44.77 g, 44.77 mL, 175.4 mmol, 44.77 g), and 1-Me-Imidazole (16.99 g, 16.48 mL, 206.9 mmol, 16.99 g). With agitation, MSA (7.66 g, 5.23 mL, 79.7 mmol, 7.66 g) was added at ~20° C., and a slight exotherm to 26° C. was observed. The reaction mixture was cooled to 10° C. and EDAC (42.73 g, 42.73 mL, 222.9 mmol, 42.73 g) was added as a solid followed by a DMF rinse (60.4 g, 63.9 mL, 826 mmol, 60.4 g). The reaction mixture was aged overnight at 10° C. with agitation. An aliquot was taken and subjected to HPLC analysis to confirm reaction completion.

The batch temperature was increased to 15° C., and 2-Me-THF (923.96 g, 10727 mmol, 100 mass %, 1080 mL, 67.31) was charged to the reactor, followed by a saturated aqueous brine solution (158 mL, 835.8 mmol, 26 mass %, 158 mL, 5.244) and an aqueous 2.0 M HCl solution (78 mL, 78 mmol, 1.0 mol/L, 78 mL, 0.49). The batch temperature was then increased to 20° C. The biphasic mixture was agitated for 15 min and allowed to settle for 5 min. An saturated aqueous brine solution (157 mL, 830.5 mmol, 26 mass %, 157 mL, 5.211) and an aqueous 2.0 M HCl solution (78 mL, 78 mmol, 1.0 mol/L, 78 mL, 0.49) were then added to the reactor. The biphasic mixture was agitated for 15 min, allowed to settle for 5 min, and the aqueous layer was removed. Water (634.6 g, 35230 mmol, 100 mass %, 634.6 mL, 221.0) was then added to the reactor. The biphasic mixture was agitated for 15 min, allowed to settle for 5 min, and the aqueous layer was removed. Next, 10 w/w % aqueous NaHCO$_3$ solution (164.2 g, 97.73 mmol, 5 mass %, 158.2 mL, 0.6132) and water (476.3 g, 26440 mmol, 100 mass %, 476.3 mL, 165.9) were added to the reactor. The biphasic mixture was agitated for 15 min, settled for 5 min, and the aqueous layer was removed. A saturated aqueous brine solution (752.9 g, 3349 mmol, 26 mass %, 633.2 mL, 21.02) was then added to the reactor. The biphasic mixture was agitated for 30 min, allowed to settle for 5 min, and the aqueous layer was removed.

The organic stream was distilled to 6 volumes (380 mL) at a pressure of 200 mbar, a jacket temperature of 60° C., and a batch temperature of ~35° C. 2-Me-THF (765 g, 8881.6 mmol, 100 mass %, 891 mL, 55.73) was charged to the reactor. The organic solution was distilled to 6 volumes (380 mL) at a pressure of 200 mbar, a jacket temperature of 60° C., and a batch temperature of ~35° C. 2-Me-THF (268.5 g, 3117 mmol, 100 mass %, 313 mL, 19.56) was charged to the reactor. The organic solution was distilled to 6 volumes (380 mL) at a pressure of 200 mbar, a jacket temperature of 60° C., and a batch temperature of ~35° C. The concentrated stream was polish filtered through a 0.4 μm PTFE filter. The reactor was rinsed with 2-Me-THF (134.6 g, 1563 mmol, 100 mass %, 157 mL, 9.806) and the rinse was passed through the PTFE filter. This solution was termed "organic solution."

To a clean, dry, 2.5 L Chemglass reactor were added LiOtBu 1.0 M in THF (9.91 g, 11.2 mmol, 1 mol/L, 11.2 mL, 0.0700) and 2-Me-THF (1633.3 g, 18963 mmol, 100 mass %, 1900 mL, 119.0). The organic solution was charged to the reactor, with agitation, over 2 hours (at a rate of ~100 mL/h) via a sim-dos pump. The reaction mixture was aged 10 minutes upon completion of the addition. An aliquot was taken and subjected to HPLC analysis to confirm reaction completion.

Acetic acid (1.03 g, 17.2 mmol, 100 mass %, 0.983 mL, 0.108) and methanol (150 g, 4681.41 mmol, 100 mass %, 189 mL, 29.37) were charged to the reactor. The organic stream was distilled to 16.5 vol Me-THF. Acetone (638.4 g, 10990 mmol, 100 mass %, 810 mL, 68.97) was added to the reactor and the organic stream was distilled to 9 vol at a pressure of 100 mbar and a jacket temperatures of less than 40° C. The organic stream was heated to 35° C., and methanol (400 g, 12483.8 mmol, 100 mass %, 505 mL, 78.33) was added. The stream was cooled to 20° C. to induce crystallization.

Heat cycles were performed for ~15 h by heating the batch to 35° C. over 20 min, holding for 10 min, cooling to 20° C. over 20 min, and holding 10 min. After the heat cycles, heptane (686 g, 6846.10 mmol, 100 mass %, 1000 mL, 42.96) was added over 4 hours via a sim-dos pump. The slurry was aged for 2 h. The product was filtered, washed with methanol (152.2 g, 4750 mmol, 100 mass %, 192 mL, 29.81) to afford 6-fluoro-5-(R)-(3-(S)-(8-fluoro-1-methyl-2,4-dioxo-1,2-dihydroquinazolin-3(4H)-yl)-2-methylphenyl)-2-(S)-(2-hydroxypropan-2-yl)-2,3,4,9-tetrahydro-1H-carbazole-8-carboxamide (68.4 g, 119 mmol, 100 mass %, 75.0% Yield, 68.4 mL, 0.750).

Process of the First Aspect

TABLE 1

Effect of Base on the Selectivity Ratio of Compound 8 to its diastereomer.

| Base | Ratio of Compound (8) to its diastereomer |
|---|---|
| lithium t-butoxide | 25:1 |
| lithium pyrrolidinoborohydride | 14.7:1 |
| lithium isopropoxide | 13.3:1 |
| lithium (dimethylamino)trihydroborate | 13.3:1 |
| lithium acetylide ethylenediamine | 13.2:1 |
| LiNH$_2$ | 12.6:1 |
| lithium borohydride | 12.6:1 |
| LiSEt | 12.2:1 |
| lithium phenoxide | 12.1:1 |
| lithium silanolate | 11.5:1 |
| LDA | 11.5:1 |
| LiNCy$_2$ | 11.4:1 |
| lithium oxide | 11.2:1 |
| LiTMP | 11.0:1 |
| LiPPh$_2$ | 10.3:1 |
| lithium hydroxide | 10.3:1 |
| lithium methoxide | 10.2:1 |
| lithium ethoxide | 10.1:1 |
| NaHMDS | 9.7:1 |
| sodium hydride | 8.8:1 |
| sodium silanolate | 8:1 |
| potassium phosphate, tribasic | 6.8:1 |
| sodium t-butoxide | 6.4:1 |
| TMPMgCl-LiCl | 5.6:1 |
| cesium carbonate | 4.9:1 |
| potassium t-butoxide | 4.1:1 |
| potassium t-pentoxide | 3.9:1 |
| KHMDS | 3.7:1 |
| potassium silanolate | 3:1 |
| NaNH$_2$ | 3:1 |
| DBU | 2.1:1 |
| TMG | 1.8:1 |

R is n-propyl;
Solvent is 1,4-dioxane.

2. Effect of Solvent on the Yield of Compound 8 to its Diastereomer.

TABLE 2

Effect of Solvent on the Selectivity Ratio

| Solvent | Selectivity Ratio of Compound (8) to its diastereomer |
|---|---|
| 1,4-dioxane | 23.5:1 |
| MeTHF | 19.5:1 |
| THP | 10.1:1 |
| CPME | 9.2:1 |
| THF | 9.2:1 |
| EtOAc | 6.8:1 |
| nBuOAc | 6.7:1 |
| IPAc | 6.6:1 |
| iBuOAc | 6.4:1 |
| MIBK | 4.3:1 |
| IPA | 2.8:1 |
| DEM | 2.3:1 |
| NMP | 2.2:1 |
| DMAc | 1.9:1 |
| DMF | 1.5:1 |
| MeOH | 1.2:1 |

R is n-propyl;
base is lithium t-butoxide

TABLE 3

Effect of Solvent Mixtures on Selectivity Ratio

| Solvent 1 (S1) | Solvent 2 (S2) | Ratio of S1/S2 | Selectivity Ratio of Compound (8) to its diastereomer |
|---|---|---|---|
| 1,4-dioxane | CPME | 4:1 | 22.4:1 |
| 1,4-dioxane | CPME | 1:1 | 19.2:1 |
| 1,4-dioxane | IPAc | 4:1 | 18.0:1 |
| 1,4-dioxane | IPAc | 1:1 | 14.6:1 |
| 1,4-dioxane | CPME | 1:4 | 12.8:1 |
| 1,4-dioxane | DEM | 4:1 | 22.0:1 |
| 1,4-dioxane | DEM | 1:1 | 16.7:1 |
| 1,4-dioxane | DEM | 1:4 | 11.7:1 |
| 1,4-dioxane | EtOAc | 4:1 | 18.7:1 |
| 1,4-dioxane | EtOAc | 1:1 | 13.4:1 |
| 1,4-dioxane | iBuOAc | 4:1 | 19.1:1 |
| 1,4-dioxane | iBuOAc | 1:1 | 14.5:1 |
| 1,4-dioxane | IPA | 4:1 | 15.4:1 |
| 1,4-dioxane | MeTHF | 4:1 | 19.3:1 |
| 1,4-dioxane | MeTHF | 1:1 | 17.3:1 |
| 1,4-dioxane | MeTHF | 1:4 | 14.9:1 |
| 1,4-dioxane | MIBK | 4:1 | 16.8:1 |
| 1,4-dioxane | MIBK | 1:1 | 10.4:1 |
| 1,4-dioxane | nBuOAc | 4:1 | 19.1:1 |
| 1,4-dioxane | nBuOAc | 1:1 | 14.3:1 |
| 1,4-dioxane | nBuOAc | 1:4 | 10.1:1 |
| 1,4-dioxane | THF | 4:1 | 18.9:1 |
| 1,4-dioxane | THF | 1:1 | 14.4:1 |
| 1,4-dioxane | THF | 1:4 | 11.2:1 |
| MeTHF | MeOAc | 4:1 | 11.1:1 |
| MeTHF | IPAc | 4:1 | 10.2:1 |
| MeTHF | CPME | 1:4 | 10.4:1 |
| THP | MeTHF | 9:1 | 10.3:1 |
| THP | MeTHF | 4:1 | 10.8:1 |
| THP | MeTHF | 1:1 | 10.3:1 |
| THP | MeTHF | 1:4 | 11.9:1 |
| THP | MeTHF | 1:9 | 11.5:1 |
| THP | nBuOAc | 4:1 | 10.2:1 |
| 1,4-dioxane | DEM | 4:1 | 3.7:1 |
| 1,4-dioxane | DMAc | 1:1 | 2.5:1 |
| 1,4-dioxane | DMAc | 1:4 | 2.0:1 |
| 1,4-dioxane | DMF | 4:1 | 3.0:1 |
| 1,4-dioxane | DMF | 1:1 | 1.9:1 |
| 1,4-dioxane | DMF | 1:4 | 1.6:1 |
| 1,4-dioxane | EtOAc | 1:4 | 8.7:1 |
| 1,4-dioxane | iBuOAc | 1:4 | 7.9:1 |
| 1,4-dioxane | IPA | 1:1 | 7.3:1 |
| 1,4-dioxane | IPA | 1:4 | 4.4:1 |
| 1,4-dioxane | IPAc | 1:4 | 9.6:1 |
| 1,4-dioxane | MeOH | 4:1 | 3.2:1 |
| 1,4-dioxane | MeOH | 1:1 | 1.5:1 |
| 1,4-dioxane | MeOH | 1:4 | 1.3:1 |
| 1,4-dioxane | MIBK | 1:4 | 6.1:1 |
| 1,4-dioxane | NMP | 4:1 | 4.1:1 |
| 1,4-dioxane | NMP | 1:1 | 2.8:1 |
| 1,4-dioxane | NMP | 1:4 | 2.4:1 |
| MeTHF | MeOAc | 1:1 | 9.3:1 |
| MeTHF | MeOAc | 1:4 | 7.0:1 |
| MeTHF | nBuOAc | 4:1 | 9.8:1 |
| MeTHF | nBuOAc | 1:1 | 9.0:1 |
| MeTHF | nBuOAc | 1:4 | 7.2:1 |
| MeTHF | IPAc | 1:1 | 8.7:1 |
| MeTHF | nBuOAc | 1:4 | 7.2:1 |
| MeTHF | IPAc | 1:1 | 8.7:1 |
| MeTHF | IPAc | 1:4 | 7.2:1 |
| MeTHF | EtOAc | 4:1 | 9.8:1 |
| MeTHF | EtOAc | 1:1 | 8.2:1 |
| MeTHF | EtOAc | 1:4 | 7.1:1 |
| MeTHF | CPME | 4:1 | 9.2:1 |
| MeTHF | CPME | 1:1 | 9.7:1 |
| THP | nBuOAc | 1:1 | 8.7:1 |
| THP | nBuOAc | 1:4 | 7.3:1 |

R is n-propyl;
base is lithium t-butoxide

3. Effect of R-Substituent on the Yield of Compound 8 to its Diastereomer.

TABLE 4

| R | Selectivity Ratio of Compound (8) to its diastereomer |
|---|---|
| Methyl | 3.8:1 |
| Ethyl | 5:1 |
| Isopropyl | 3.4:1 |
| n-Propyl | 6:1 |
| Benzyl | 2.7:1 |
| Phenyl | 1:1.5 |

1M tetrahydrofuran, 0.35 to 0.45 eq. KOtBu in THF, 20 to 30° C.

Comparative Process Disclosed in U.S. Pat. No. 9,334,290

Intermediates 25 and 26

(R)-5-Bromo-6-fluoro-2-(2-hydroxypropan-2-yl)-2,3,4,9-tetrahydro-1H-carbazole-8-carboxamide (I-25), and (S)-5-Bromo-6-fluoro-2-(2-hydroxypropan-2-yl)-2,3,4,9-tetrahydro-1H-carbazole-8-carboxamide (I-26)

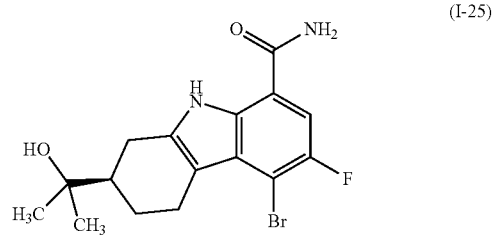

(I-25)

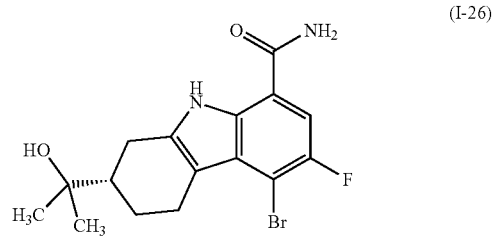

(I-26)

A sample of racemic 5-bromo-6-fluoro-2-(2-hydroxypropan-2-yl)-2,3,4,9-tetrahydro-1H-carbazole-8-carboxamide [Intermediate 24] was separated by chiral super-critical fluid chromatography as follows: column: CHIRALPAK® OD-H (3×25 cm, 5 μm); Mobile Phase: $CO_2$—MeOH (70:30) at 150 mL/min, 40° C. The first peak eluting from the column provided (R)-5-bromo-6-fluoro-2-(2-hydroxypropan-2-yl)-2,3,4,9-tetrahydro-1H-carbazole-8-carboxamide [Intermediate 25]. The second peak eluting from the column provided (S)-5-bromo-6-fluoro-2-(2-hydroxypropan-2-yl)-2,3,4,9-tetrahydro-1H-carbazole-8-carboxamide [Intermediate 26]. The mass spectra and $^1$H NMR spectra of the two enantiomers were the same. Mass spectrum m/z 369, 371 (M+H)$^+$. $^1$H NMR (500 MHz, DMSO-$d_6$) δ 10.96 (s, 1H), 8.07 (br. s., 1H), 7.55 (d, J=10.3 Hz, 1H), 7.50 (br. s., 1H), 4.24 (s, 1H), 3.26 (dd, J=15.8, 4.4 Hz, 1H), 2.93 (dd, J=17.1, 4.6 Hz, 1H), 2.72 (t, J=11.7 Hz, 1H), 2.48-2.40 (m, 1H), 2.12 (d, J=9.2 Hz, 1H), 1.70-1.62 (m, 1H), and 1.32 (qd, J=12.4, 5.3 Hz, 1H).

Alternative SFC Separation to Give Intermediate 26:

CHIRALPAK® AD-H (3×25 cm, 5 μm); Mobile Phase: $CO_2$—MeOH (55:45) at 150 mL/min, 40° C. The first peak eluting from the column provided (S)-5-bromo-6-fluoro-2-(2-hydroxypropan-2-yl)-2,3,4,9-tetrahydro-1H-carbazole-8-carboxamide [Intermediate 26]. The second peak eluting from the column provided (R)-5-bromo-6-fluoro-2-(2-hydroxypropan-2-yl)-2,3,4,9-tetrahydro-1H-carbazole-8-carboxamide [Intermediate 25].

Example 28

6-Fluoro-5-(R)-(3-(S)-(8-fluoro-1-methyl-2,4-dioxo-1,2-dihydroquinazolin-3(4H)-yl)-2-methylphenyl)-2-(S)-(2-hydroxypropan-2-yl)-2,3,4,9-tetrahydro-1H-carbazole-8-carboxamide (Single Atropisomer)

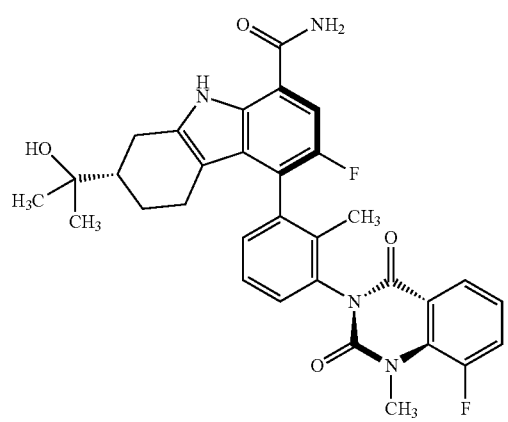

(28)

Following the procedure used to prepare Example 27, (S)-5-bromo-6-fluoro-2-(2-hydroxypropan-2-yl)-2,3,4,9-tetrahydro-1H-carbazole-8-carboxamide (single enantiomer) [Intermediate 26] (0.045 g, 0.122 mmol) and 8-fluoro-1-methyl-3-(S)-(2-methyl-3-(4,4,5,5-tetramethyl-1,3,2-dioxaborolan-2-yl)phenyl)quinazoline-2,4(1H,3H)-dione [Intermediate 10] (0.065 g, 0.158 mmol) were converted into 6-fluoro-5-(3-(S)-(8-fluoro-1-methyl-2,4-dioxo-1,2-dihydroquinazolin-3(4H)-yl)-2-methylphenyl)-2-(S)-(2-hydroxypropan-2-yl)-2,3,4,9-tetrahydro-1H-carbazole-8-carboxamide (mixture of two atropisomers) as a yellow solid (0.035 g, 49% yield). Separation of a sample of this material by chiral super-critical fluid chromatography, using the conditions used to separate Example 27, provided (as the first peak to elute from the column) 6-fluoro-5-(R)-(3-(S)-(8-fluoro-1-methyl-2,4-dioxo-1,2-dihydroquinazolin-3 (4H)-yl)-2-methylphenyl)-2-(S)-(2-hydroxypropan-2-yl)-2,3,4,9-tetrahydro-1H-carbazole-8-carboxamide. The chiral purity was determined to be greater than 99.5%. The relative and absolute configurations were determined by x-ray crystallography. Mass spectrum m/z 573 (M+H)$^+$. $^1$H NMR (500 MHz, DMSO-$d_6$) δ 10.77 (s, 1H), 8.05 (br. s., 1H), 7.94 (dd, J=7.9, 1.2 Hz, 1H), 7.56-7.52 (m, 1H), 7.43 (br. s., 1H), 7.40-7.36 (m, 1H), 7.35-7.30 (m, 2H), 7.28 (dd, J=7.5, 1.4 Hz, 1H), 4.15 (s, 1H), 3.75-3.70 (m, 3H), 2.90 (dd, J=16.8, 4.6 Hz, 1H), 2.47-2.39 (m, 1H), 1.93-1.82 (m, 3H), 1.74 (s, 3H), 1.57 (td, J=11.7, 4.2 Hz, 1H), 1.16-1.11 (m, 1H), and 1.10 (d, J=1.9 Hz, 6H). [α]$_D$: +63.8° (c 2.1, CHCl$_3$). DSC melting point onset temperature=202.9° C. (heating rate=10° C./min.).

Alternative Synthesis of Example 28:

A mixture of (S)-5-bromo-6-fluoro-2-(2-hydroxypropan-2-yl)-2,3,4,9-tetrahydro-1H-carbazole-8-carboxamide [Intermediate 26] (5.00 g, 13.54 mmol), 8-fluoro-1-methyl-3-(S)-(2-methyl-3-(4,4,5,5-tetramethyl-1,3,2-dioxaborolan-2-yl)phenyl)quinazoline-2,4(1H,3H)-dione [Intermediate 10] (6.67 g, 16.25 mmol), tripotassium phosphate (2 M in water) (20.31 mL, 40.6 mmol), and tetrahydrofuran (25 mL) was subjected to 3 evacuate-fill cycles with nitrogen. The mixture was treated with 1,1'-bis(di-tert-butylphosphino)ferrocene palladium dichloride (0.441 g, 0.677 mmol) and the mixture was subjected to 2 more evacuate-fill cycles with nitrogen. The mixture was stirred at room temperature overnight, then was diluted with EtOAc, washed sequentially with water and brine, and dried and concentrated. The residue was purified by column chromatography on silica gel, eluting with EtOAc-hexanes (sequentially 50%, 62%, 75% and 85%), to provide 6-fluoro-5-(3-(8-fluoro-1-methyl-2,4-dioxo-1,2-dihydroquinazolin-3-(S)-3(4H)-yl)-2-methylphenyl)-2-(S)-(2-hydroxypropan-2-yl)-2,3,4,9-tetrahydro-1H-carbazole-8-carboxamide as a white solid (6.58 g, 85% yield).

Material prepared by this method (40.03 g, 69.9 mmol) was separated by chiral super-critical fluid chromatography to give (2S,5R)-6-fluoro-5-(3-(8-fluoro-1-methyl-2,4-dioxo-1,2-dihydroquinazolin-3(4H)-yl)-2-methylphenyl)-2-(S)-(2-hydroxypropan-2-yl)-2,3,4,9-tetrahydro-1H-carbazole-8-carboxamide. Further purification was achieved by suspending this material in methanol, sonicating for 5 min, collection of the solid by filtration, rinsing the collected solid with methanol and drying at room temperature under reduced pressure to give a white solid (22.0 g, 90% yield). Comparison of the Overall Yields of Synthesis Steps in FIGS. 1 and 4.

TABLE 5

Yields of Processes to Prepare
Compound 6, Compound 7, and Compound 8

| Synthesis Steps in FIG. 1 | Yield |
|---|---|
| Compound 5 + Intermediate B2 → Compound 6 | 86% |
| Compound 6 + Intermediate C3 → Compound 7 | 94% |
| Compound 7 → Compound 8 | 89.4% |
| Overall Yield | 72% |

TABLE 6

Yields of Processes to Prepare Examples 27 and 28
disclosed in U.S. Pat. No. 9,334,290

Figure 4:
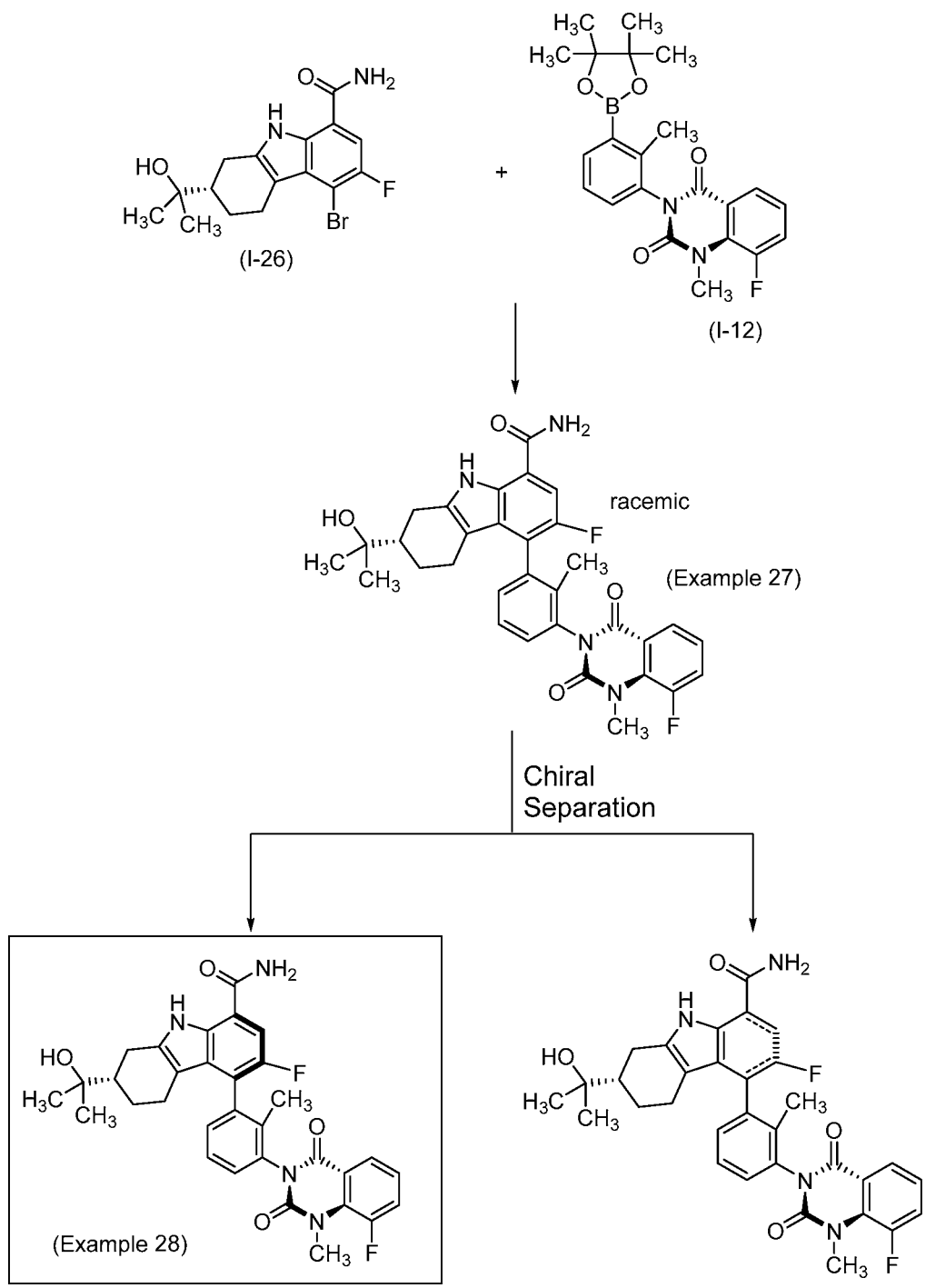
FIG. 4 shows the synthesis scheme disclosed in U.S. Pat. No. 9,334,290 for the preparation of Compound 8 from the coupling reaction of 8-fluoro-1-methyl-3-(S)-(2-methyl-3-(4,4,5,5-tetramethyl-1,3,2-dioxaborolan-2-yl) phenyl)quinazoline-2,4(1H,3H)-dione, Intermediate 10, and (S)-5-bromo-6-fluoro-2-(2-hydroxypropan-2-yl)-2,3,4,9-tetrahydro-1H-carbazole-8-carboxamide, Compound 5, to provide a racemic mixture of Example 27 in U.S. Pat. No. 9,334,290; and the chiral separation of Example 27 to provide Compound 8.

| Synthesis Steps in FIG. 4 | Yield | Yield*** |
|---|---|---|
| Intermediate I-26* + Intermediate I-10 → Example 27 | 49% | 85% |
| Chiral separation of Example 27 → Example 28** | 50% (max) | 50% (max) |
| Overall Yield | 24.5% (max) | 42.5% (max) |

*Intermediate I-26 in U.S. Pat. No. 9,334,290 is equivalent to Compound 5.
**Example 28 in U.S. Pat. No. 9,334,290 is equivalent to Compound 8.
***Alternative Process disclosed in Example 28 of U.S. Pat. No. 9,334,290.

Applicants have discovered a new synthesis processes for the preparation of 6-fluoro-5-(R)-(3-(S)-(8-fluoro-1-methyl-2,4-dioxo-1,2-dihydroquinazolin-3(4H)-yl)-2-methylphenyl)-2-(S)-(2-hydroxypropan-2-yl)-2,3,4,9-tetrahydro-1H-carbazole-8-carboxamide from Compound 5. The new processes provide higher overall yield compared to the processes disclosed in U.S. Pat. No. 8,334,290. Additionally, the new processes do not require chiral separation of a racemic mixture.

What is claimed is:
1. A process for preparing Compound 8:

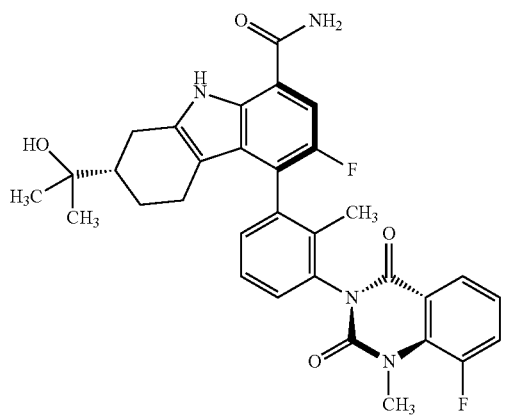

comprising the step of reacting Compound 7:

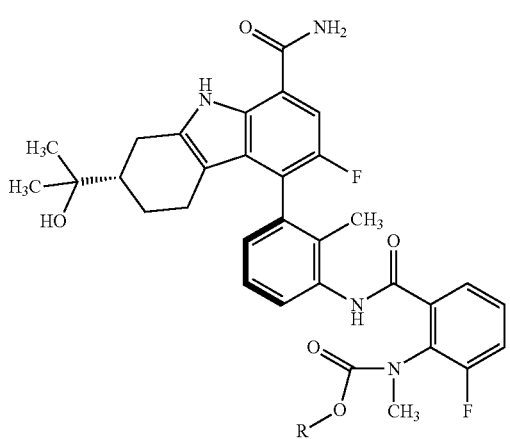

wherein R is $C_{1-8}$ alkyl or benzyl;
in the presence of:
(i) one or more bases selected from lithium bases, sodium bases, potassium bases, cesium bases, 1,8-diazabicycloundec-7-ene, and 1,1,3,3-tetramethylguanidine; and
(ii) a solvent selected from n-butyl acetate, cyclopentyl methyl ether, dimethoxyethane, dimethylacetamide, dimethylformamide, 1,4-dioxane, ethyl acetate, isobutyl acetate, isopropyl acetate, isopropyl alcohol, methanol, methyl acetate, methyl isobutyl ketone, N-methyl-2-pyrrolidone, 2-methyltetrahydrofuran, tetrahydrofuran, tetrahydropyran, and mixtures thereof;
to provide said Compound 8.

2. The process according to claim 1 wherein said base is lithium tert-butoxide; and
(ii) said solvent is selected from 1,4-dioxane, 2-methyltetrahydrofuran, tetrahydropyran, and mixtures thereof.

3. The process according to claim 1 having a selectivity yield of at least 60% Compound 8 compared to its diastereomer.

4. The process according to claim 1, wherein said Compound (7) is prepared by reacting Compound 6 or a salt thereof with Intermediate C3 or a salt thereof:

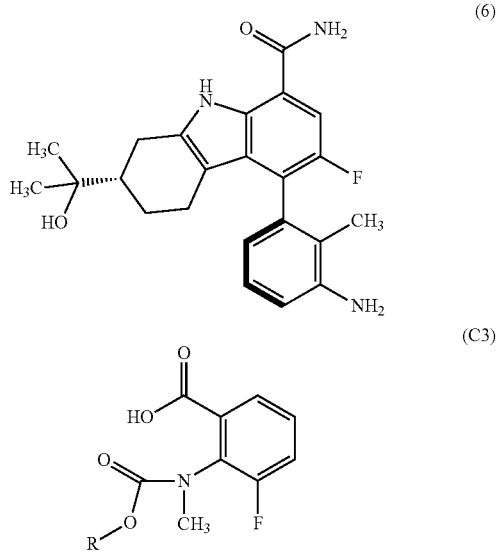

in the presence of:
(i) an adjuvant selected from O-(benzotriazol-1-yl)-N,N,N',N'-tetramethyluronium tetrafluoroborate, 1-[bis(dimethylamino)methylene]-1H-1,2,3-triazolo[4,5-b]pyridinium 3-oxide hexafluorophosphate, 1-ethyl-3-(3-dimethylaminopropyl) carbodiimide, 2-hydroxypyridine-N-oxide, and mixtures thereof;
(ii) a base selected from diisopropylethylamine, 1-methylimidazole, 3,4-lutidine, pyridine, 4-picoline, 2,6-lutidine, dimethylaminopyridine, N-methylmorpholine, tributyl amine, N-methylpyrrolidine, and mixtures thereof;
(iii) an acid selected from methanesulfonic acid, ethanesulfonic acid, toluenesulfonic acid, hydrochloric acid, and mixtures thereof;
(iv) an organic solvent selected from dimethylformamide, N-methyl-2-pyrrolidone, dimethylacetamide, dimethylsulfoxide, tetrahydrofuran, acetonitrile, 2-methyltetrahydrofuran, and mixtures thereof; and
(v) water;
at a temperature in the range of from about 0° C. to about 20° C.; to provide said Compound 7.

5. The process according to claim 4, wherein said Compound (6) is prepared by reacting Compound 5 or a salt thereof with Intermediate B1 or a salt thereof:

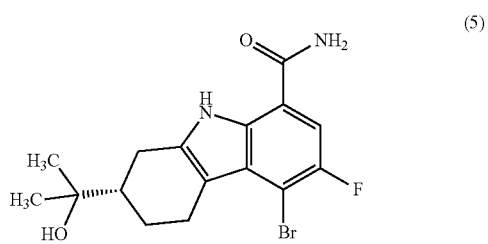

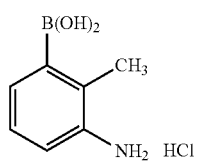

(B1)

in the presence of:
(i) one or more catalysts selected from palladium(II) acetate, bis(acetonitrile)dichloropalladium(II), and allylpalladium(II) chloride dimer;
(ii) a ligand selected from (R)-(+)-7,7'-bis[di(3,5-dimethylphenyl)phosphino]-1,1'-spirobiindane, (R)-(+)-2,2'-bis(di-p-tolylphosphino)-1,1'-binaphthyl, (R)-(+)-2,2'-bis[di(3,5-xylyl)phosphino]-1,1'-binaphthyl, (R)-(+)-2,2'-bis(diphenylphosphino)-1,1'-binaphthyl, (2'-(diphenylphosphino)-[1,1'-binaphthalen]-2-yl)diphenylphosphine oxide, and bis{2-[(11bR)-3,5-dihydro-4H-dinaphtho[2,1-c:1',2'-e]phosphepin-4-yl]ethyl}amine;
(iii) a base selected from LiOH, NaOH, KOH, $K_3PO_4$, and mixtures thereof; and
(iv) a solvent selected from methyl tetrahydrofuran, methanol, acetonitrile, dioxane, isopropyl alcohol, t-amyl alcohol, and mixtures thereof;

at a temperature in the range of from about 5 to about 20° C.; to provide said Compound 6 or a salt thereof.

6. Compound C3 having the structure:

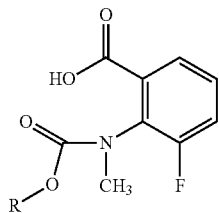

(C3)

wherein R is $C_{1-8}$ alkyl or benzyl.

* * * * *

UNITED STATES PATENT AND TRADEMARK OFFICE
CERTIFICATE OF CORRECTION

PATENT NO. : 10,875,843 B2
APPLICATION NO. : 16/471020
DATED : December 29, 2020
INVENTOR(S) : Ronald Carrasquillo-Flores et al.

It is certified that error appears in the above-identified patent and that said Letters Patent is hereby corrected as shown below:

On the Title Page

Item (56) Column 2 (Other Publications), Line 1, Delete "Quinasolinediones"," and insert -- Quinazolinediones", --, therefor.

Item (56) Column 2 (Other Publications), Line 7, Delete "1H-carbezole-8-" and insert -- 1H-carbazole-8- --, therefor.

Signed and Sealed this
Twenty-first Day of September, 2021

Drew Hirshfeld
*Performing the Functions and Duties of the*
*Under Secretary of Commerce for Intellectual Property and*
*Director of the United States Patent and Trademark Office*